United States Patent
Khairkhahan et al.

(10) Patent No.: US 7,056,294 B2
(45) Date of Patent: Jun. 6, 2006

(54) METHOD AND APPARATUS FOR ACCESSING THE LEFT ATRIAL APPENDAGE

(75) Inventors: Alexander K. Khairkhahan, Palo Alto, CA (US); Andrew G. C. Frazier, Mountain View, CA (US); Alan R. Klenk, San Jose, CA (US); Marc S. Kreidler, Sunnyvale, CA (US); Stewart M. Kume, Belmont, CA (US); Darrell H. Ogi, Sunnyvale, CA (US); Chad C. Roue, Fremont, CA (US); Erik J. van der Burg, Sunnyvale, CA (US)

(73) Assignee: ev3 Sunnyvale, Inc, Plymouth, MN (US)

( * ) Notice: Subject to any disclaimer, the term of this patent is extended or adjusted under 35 U.S.C. 154(b) by 239 days.

(21) Appl. No.: 10/100,270

(22) Filed: Mar. 15, 2002

(65) Prior Publication Data

US 2002/0169377 A1 Nov. 14, 2002

Related U.S. Application Data

(63) Continuation-in-part of application No. 09/549,218, filed on Apr. 13, 2000, now Pat. No. 6,650,923.

(51) Int. Cl.
*A61B 5/00* (2006.01)
*A61M 25/00* (2006.01)

(52) U.S. Cl. .............. 600/585; 600/435; 606/167; 604/264

(58) Field of Classification Search ........ 600/433–435, 600/585; 604/22, 264, 164.01, 164.1, 164.11, 604/523, 164; 606/166, 167, 185, 18
See application file for complete search history.

(56) References Cited

U.S. PATENT DOCUMENTS

| 3,811,449 A | 5/1974 | Gravlee |
| 4,175,545 A | 11/1979 | Termanini |
| 4,718,417 A | 1/1988 | Kittrell et al. |
| 4,759,348 A | 7/1988 | Cawood |
| 4,827,907 A | 5/1989 | Tashiro |
| 4,960,412 A | 10/1990 | Fink |
| 4,966,150 A | 10/1990 | Etienne et al. |
| 4,998,972 A | 3/1991 | Chin et al. |

(Continued)

FOREIGN PATENT DOCUMENTS

FR 2 481 917 11/1981

(Continued)

OTHER PUBLICATIONS

*Transeptal Left Heart Catheterization: Usefulness of the Intracavity Electrocardiogram in the Localization of the Fossa Ovalis*, Hector Bidoggia, MD, Juan P. Maciel, MD, and Jose A. Alvarez, MD, *Catheterization and Cardiovascular Diagnosis* 24-221-225 (1991).

(Continued)

*Primary Examiner*—Charles Marmor
(74) *Attorney, Agent, or Firm*—Knobbe Martens Olson & Bear LLP

(57) ABSTRACT

Disclosed is an apparatus for facilitating access to the left atrium, and specifically the left atrial appendage. The apparatus may comprise a sheath with first and second curved sections that facilitate location of the fossa ovalis and left atrial appendage. The apparatus may further comprise tissue piercing and dilating structures. Methods are also disclosed.

27 Claims, 18 Drawing Sheets

U.S. PATENT DOCUMENTS

| | | | |
|---|---|---|---|
| 5,108,413 A * | 4/1992 | Moyers | 606/191 |
| 5,312,341 A | 5/1994 | Turi | |
| 5,427,119 A | 6/1995 | Swartz et al. | |
| 5,497,774 A | 3/1996 | Swartz et al. | |
| 5,499,975 A | 3/1996 | Cope et al. | |
| 5,514,236 A * | 5/1996 | Avellanet et al. | 156/154 |
| 5,558,093 A | 9/1996 | Pomeranz | |
| 5,558,652 A | 9/1996 | Henke | |
| 5,643,231 A | 7/1997 | Lurie et al. | |
| 5,690,611 A * | 11/1997 | Swartz et al. | 604/528 |
| 5,715,818 A * | 2/1998 | Swartz et al. | 600/374 |
| 5,722,400 A | 3/1998 | Ockuly et al. | |
| 5,724,975 A | 3/1998 | Negus et al. | |
| 5,725,512 A | 3/1998 | Swartz et al. | |
| 5,772,678 A * | 6/1998 | Thomason et al. | 606/185 |
| 5,807,261 A | 9/1998 | Benaron et al. | |
| 5,814,028 A | 9/1998 | Swartz et al. | |
| 5,814,029 A | 9/1998 | Hassett | |
| 5,820,591 A | 10/1998 | Thompson et al. | |
| 5,833,673 A | 11/1998 | Ockuly et al. | |
| 5,840,027 A | 11/1998 | Swartz et al. | |
| 5,848,969 A | 12/1998 | Panescu et al. | |
| 5,865,791 A | 2/1999 | Whayne et al. | |
| 5,879,296 A | 3/1999 | Ockuly et al. | |
| 6,004,280 A | 12/1999 | Buck et al. | |
| 6,066,126 A | 5/2000 | Li et al. | |
| 6,090,084 A | 7/2000 | Hasset et al. | |
| 6,152,144 A | 11/2000 | Lesh et al. | |
| 6,156,018 A | 12/2000 | Hassett | |
| 6,203,531 B1 | 3/2001 | Ockuly et al. | |
| 6,231,561 B1 | 5/2001 | Frazier et al. | |
| 6,285,898 B1 | 9/2001 | Ben-Haim | |
| 6,290,674 B1 | 9/2001 | Roue et al. | |
| 6,328,727 B1 | 12/2001 | Frazier et al. | |
| 6,419,669 B1 | 7/2002 | Frazier et al. | |
| 6,551,303 B1 | 4/2003 | Van Tassel et al. | |
| 6,650,923 B1 | 11/2003 | Lesh et al. | |
| 2003/0144657 A1* | 7/2003 | Bowe et al. | 606/41 |

FOREIGN PATENT DOCUMENTS

| | | |
|---|---|---|
| SU | 1297782 AL1 | 3/1987 |
| WO | WO 200010452 A1 * | 3/2000 |
| WO | WO 00/27292 | 5/2000 |

OTHER PUBLICATIONS

International Search Report from PCT/US03/08044 dated Dec. 11, 2003.

* cited by examiner

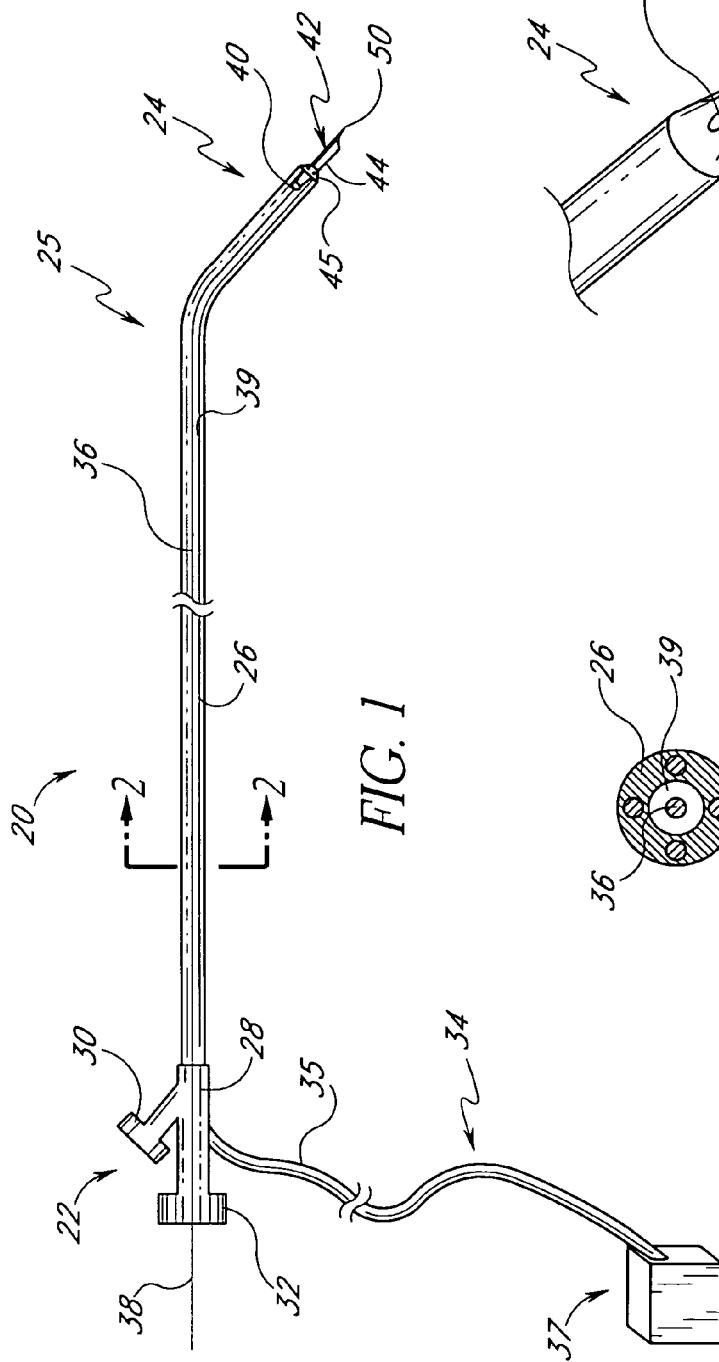
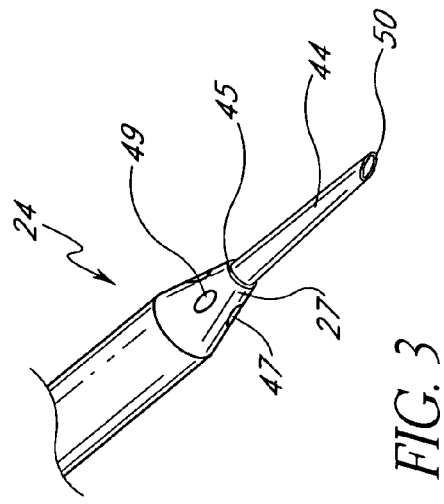
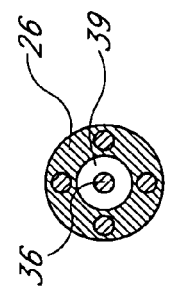
FIG. 1
FIG. 2
FIG. 3

METHOD AND APPARATUS FOR ACCESSING THE LEFT ATRIAL APPENDAGE

This is a continuation-in-part of U.S. patent application Ser. No. 09/549,218, filed Apr. 13, 2000 now U.S. Pat. No. 6,650,923, the disclosure of which is incorporated in its entirety herein by reference.

BACKGROUND OF THE INVENTION

The present invention relates to transseptal access systems for accessing the left atrium from the right atrium such as by crossing the fossa ovalis.

The typical human heart includes a right ventricle, a right atrium, left ventricle and left atrium. The right atrium is in fluid communication with the superior vena cava and the inferior vena cava. The tricuspid valve separates the right atrium from the right ventricle. On the inner wall of the right atrium where it is separated from the left atrium is a thin walled, recessed portion, the fossa ovalis. In the heart of a fetus, the fossa ovalis is open (patent foramen), permitting fetal blood to flow between the right and left atria, bypassing the fetal lungs in favor of the placental blood flow. In most individuals, this opening closes after birth. In as many as about 20 percent of adults an opening (the patent foramen) still remains in place of the fossa ovalis between the right and left atria.

A wide variety of diagnostic and therapeutic procedures have been developed in which a catheter is transluminally advanced into various chambers and across valves of the heart. The most difficult chamber of the heart to access with a catheter is the left atrium. Access to the left atrium through the pulmonary artery is not possible. Approaches from the left ventricle are difficult, may cause arrhythmias and may present difficulty in obtaining stable catheter positioning. Accordingly, the presently preferred method of accessing the left atrium is through a transseptal approach, achieved by catheterization of the right atrium with subsequent penetration of the interatrial septum. The reduced wall thickness and location of the fossa ovalis makes it a useful access point for a transseptal access puncture.

A variety of risks are attendant to transseptal catheterization, in addition to the risks associated with normal heart catheterization. The primary additional risk is that associated with inaccurate identification and localization of the atrial septum and the fossa ovalis in particular. Improper placement of the catheter tip prior to the transseptal puncture presents the risk of puncture of tissue other than the interatrial septum, such as the aorta and the posterior wall of the right or left atrium. For this reason, catheterization is accompanied by fluoroscopy or other visualizing techniques to assist in properly locating the catheter tip in relation to the septum.

The objectives of left atrial access can be either diagnostic or therapeutic. One diagnostic use is pressure measurement in the left atrium. In the setting of an obstructed mitral valve (mitral stenosis), left atrial access allows a determination of the pressure difference between the left atrium and left ventricle. Left atrial access also allows entry into the left ventricle through the mitral valve. This is desirable when an artificial aortic valve is in place. The advent of aortic valve replacement with mechanical artificial valves, and the increase in the aged population and growing longevity of that population subsequent to aortic valve replacement, brings a greater need to evaluate the late stage functionality of such artificial valves.

Diagnostic measurement of the left ventricular pressures are, therefore, desirable to allow evaluation of mechanical artificial aortic valves post-replacement. It may be unsafe to cross these mechanical artificial valves retrograde from the aorta; therefore, access to the left ventricle by the antegrade route using a transseptal puncture is the preferred approach. Once a catheter has been placed in the left atrium using the transseptal approach, access to the left ventricle can be gained by advancing catheters across the mitral valve.

Many diagnostic indications exist for left atrial pressure measurements in addition to evaluating the functionality of artificial mitral valves. Other diagnostic indications for accessing the left ventricle via the antegrade transseptal approach include aortic stenosis, when a cardiologist is unable to pass a catheter retrograde into the left ventricle, and some disease states where the antegrade approach is considered preferable, such as subaortic obstruction.

Presently, the therapeutic objectives of left atrial access are primarily two-fold. The first is mitral valvuloplasty which represents an alternative to surgical procedures to relieve obstruction of the mitral valve. The second therapeutic objective is for electrophysiological intervention in the left atrium. Catheter ablation involves the placement of energy (typically RF) through a catheter, into various locations of the heart to eradicate inappropriate electrical pathways affecting the heart function. When these locations are in the left atrium, the catheter through which the radio frequency generator is placed typically is itself placed with transseptal catheterization. More recently, therapeutic treatment of the left atrial appendage (LAA) to reduce the risk of embolic stroke has also been proposed.

Despite clinical acceptance of a wide variety of procedures which require access to the left atrium, significant room for improvement remains in the actual access technique. For example, the step of locating an appropriate site on the septum such as the fossa ovalis is highly technique dependant and can be inaccurate. This increases procedure time, and creates a risk that the needle will pierce the heart wall in an unnecessary and potentially undesirable location. Thus, there remains a need for a device and method for quickly and accurately locating and piercing the fossa ovalis to permit rapid and accurate transseptal access.

SUMMARY OF THE INVENTION

In accordance with one aspect of the present invention, there is provided a transseptal access sheath comprising; a first curved section, and a second curved section; the first curved section having an outer edge that defines a first proximal edge point, and a first distal edge point, wherein the intersection between a tangent drawn to the first curved section at the first proximal edge point and a tangent drawn to the first curved section at the first distal edge point, define a first angle and a first plane; the second curved section having an outer edge that defines a second proximal edge point, and a second distal edge point; wherein the intersection between a tangent drawn to the second curved section at the second proximal edge point and a tangent drawn to the second curved section at the second distal edge point, define a second angle and a second plane; wherein the first angle is within the range of about 60 to about 120 degrees; wherein the second angle is within the range of about 0 and about 180 degrees, more preferably about 60 and about 120 degrees; and wherein the angle between the first and second plane is within the range of about 60 and about 120 degrees.

In accordance with another aspect of the present invention, there is provided a transseptal access sheath comprising; a first curved section, and a second curved section; wherein the first curved section is shaped to abut the interior wall of the right atrium substantially opposite the fossa ovalis while directing the distal tip toward the fossa ovalis; and, wherein the second curved section is shaped to facilitate location and access of a desired region of the LAA.

In accordance with another aspect of the present invention, there is provided a transseptal access system comprising a sheath, a dilator and a needle; wherein the sheath comprises; a first curved section, and a second curved section; the first curved section having an outer edge that defines a first proximal edge point, and a first distal edge point, wherein the intersection between a tangent drawn to the first curved section at the first proximal edge point and a tangent drawn to the first curved section at the first distal edge point, define a first angle and a first plane; the second curved section having an outer edge that defines a second proximal edge point, and a second distal edge point wherein the intersection between a tangent drawn to the second curved section at the second proximal edge point and a tangent drawn to the second curved section at the second distal edge point, define a second angle and a second plane; wherein the first angle is within the range of about 90 degrees; wherein the second angle is within the range of about 90 degrees; and wherein the angle between the first and second plane is within the range of about 90 degrees.

BRIEF DESCRIPTION OF THE DRAWINGS

FIG. 1 is a side elevational schematic view of a transseptal access system in accordance with the present invention.

FIG. 2 is a cross-sectional view taken along the line 2—2 in FIG. 1.

FIG. 3 is an enlarged perspective view of the distal end of the transseptal access system of FIG. 1.

DETAILED DESCRIPTION OF THE PREFERRED EMBODIMENT

Figure 4:
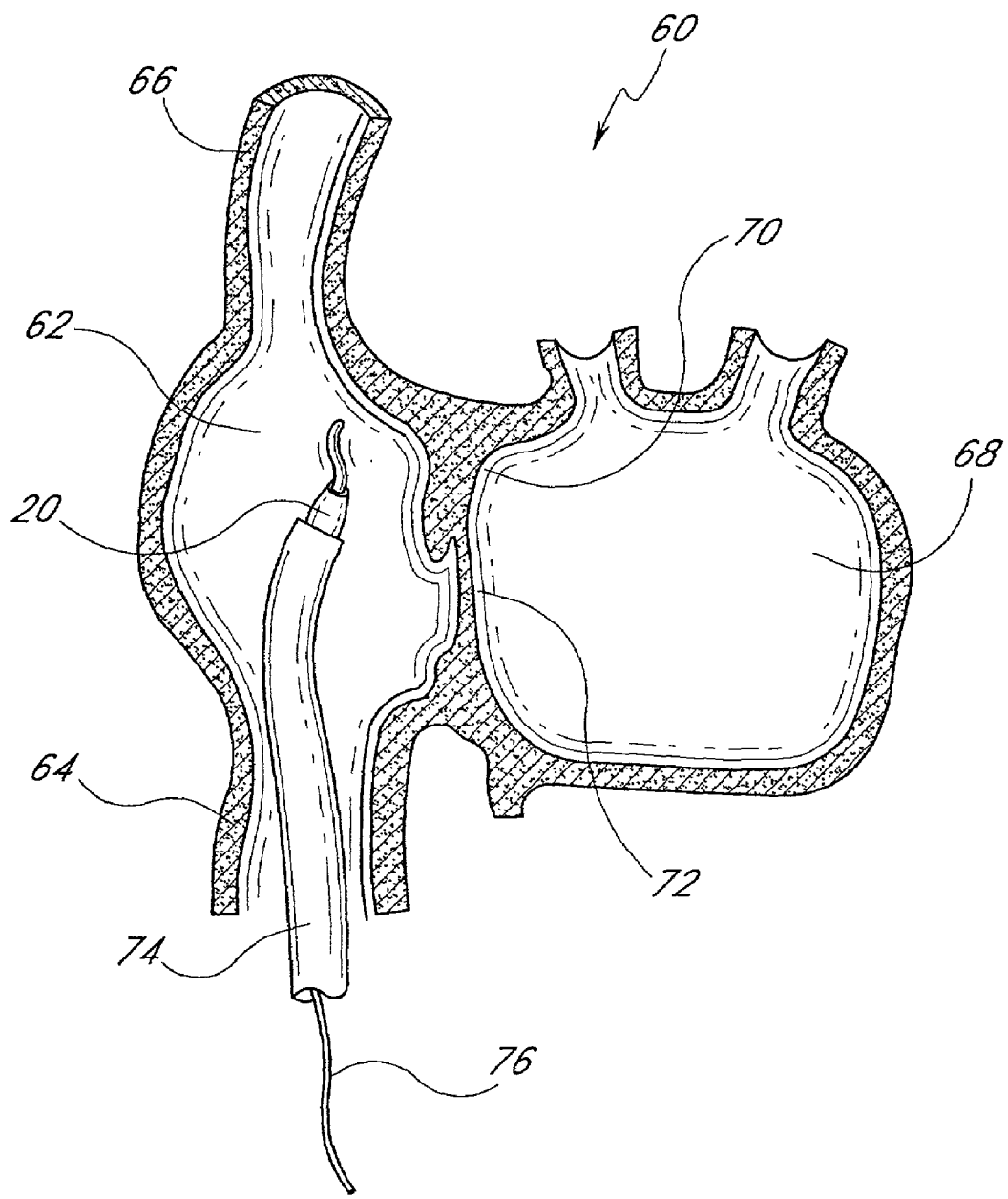
FIG. 4 is a schematic cross-sectional view of a portion of the heart, showing a transseptal access catheter of the present invention within the right atrium.

Referring to FIG. 1, there is disclosed a dilator 20 in accordance with the present invention. Dilator 20 has a proximal end 22, a distal end 24 and an elongate flexible tubular body 26. The overall length of the dilator 20 depends upon the percutaneous access point and the desired application. For example, lengths in the area of from about 80 cm to about 100 cm are typical for use in percutaneous transluminal access at the femoral vein for locating and puncturing a site on the atrial septum in the heart.

Tubular body 26 may be manufactured in accordance with any of a variety of known techniques, for manufacturing catheters adapted to reach the coronary arteries or chambers of the heart. For example, tubular body 26 may be manufactured as an extrusion of appropriate biocompatible polymeric materials such as high density polyethylene, polytetrafluoroethylene (PTFE), nylons, and a variety of others which are known in the art. Blended materials may also be used, such as HDPE (e.g., HDPE/LDPE ratios such as 50%:50%, 60%:40% and others) with from about 5% to about 25%, and, in one embodiment, about 20% $BaSO_4$ for lubricity and radiopacity. Alternatively, at least a portion or all of the length of tubular body 26 may comprise a spring coil, solid walled hypodermic needle tubing (e.g., stainless steel, NiTi alloys) or braided reinforced wall as is understood in the catheter and guidewire arts.

For most applications, the tubular body 26 is provided with an approximately circular cross sectional configuration having an outside diameter within the range of from about 0.020 inches to about 0.200 inches. In accordance with one embodiment of the invention, the tubular body 26 has an outside diameter of about 0.160 inches throughout its length. Other lengths and diameters may be readily utilized, depending upon the desired profile and performance characteristics.

The proximal end 22 is provided with a manifold 28, having one or more access ports as in known in the art. In the illustrated embodiment, manifold 28 is provided with a core wire port 32 which may also or alternatively function as a guidewire port in an over the wire embodiment. An injection port 30 may also be provided, for injecting a contrast media, such as to confirm that the distal end 24 has traversed the intraatrial septum. Additional access ports may be provided as needed, depending upon the functional capabilities of the catheter. Manifold 28 may be injection molded from any of a variety of medical grade plastics or formed in accordance with other techniques known in the art.

The proximal end 22, either at the manifold 28 or distally of the manifold 28 is also provided with a communication line 34 such as a fiber optic bundle 35 in accordance with one aspect of the present invention. In one embodiment of the invention, fiber optic bundle or signal transmitting line 35 communicates with a signal e.g. sound, light, ultrasonic or other vibration, etc.) generator and detector 37. In this embodiment of the invention, the detector 37 enables the catheter to distinguish among solid tissue or a thick membrane, a thin membrane such as at the fossa ovalis, and right atrial or left atrial chamber blood beyond the distal end 24 of dilator 20 as will be discussed.

The flexible body 26 is provided with a preset bend 25, for assisting in biasing the distal end 24 against the intraatrial septum as is understood in the art. Bend 25 preferably has a radius within the range of from about 0.5 cm to about 5 cm and, in one embodiment, about 2.5 cm. Bend 25 is centered on a point which is within the range of from about 1 cm to about 10 cm proximally from distal end 24. In one embodiment, the bend 25 is centered at approximately 6 cm proximally from distal end 24. The bend 25 is defined by a proximal transition where it meets the substantially linear proximal portion of the dilator 20, and a distal transition where it meets the substantially linear distal portion of the dilator 20. The angular deflection of the bend 25 is generally within the range of from about 30° to about 80° and, in one embodiment, is about 50°.

Bend 25 may be provided in accordance with any of a variety of techniques. For example, in an embodiment of tubular body 26 which includes a hypotube or other metal tubing, the tubular body 26 may be bent such as around a forming mandrel in excess of the elastic limit of the hypotube. Alternatively, an injection molded catheter body may be heat set in a predetermined bend, such as with removable flexible mandrels extending through any interior lumen to maintain patency of the lumen around the bend. Other techniques will be known to those of skill in the art. Alternatively, the bend 25 may be formed during or after placement of the catheter in the heart. This may be accomplished by providing the catheter with any of a variety of steering mechanisms, which allow a distal portion of the catheter to be inclined away from the axis of the normal bias of the catheter. For example, one or more axially moveable pull wires may extend throughout the length of the catheter. Proximal traction on a pull wire which is secured at the distal end of the catheter will cause a lateral deflection of the catheter.

Referring to the enlarged schematic illustration of FIG. 3, distal end 24 is provided with at least one signal transmitting surface 47 and at least one signal receiving surface 49. Transmitting surface 47 is adapted to transmit a signal from the distal end 24 of dilator 20 and generally in the distal direction with respect to the dilator. Receiving surface 49 is adapted for receiving a reflected return signal traveling in a generally proximal direction with respect to the distal end 24 of dilator 20. In one embodiment, the transmitting surface 47 comprises the distal end of a fiber optic or fiber optic bundle, or a transparent window positioned at the distal end of a fiber optic or fiber optic bundle. Similarly, the receiving surface 49 comprises a distal end of a receiving fiber optic or a transparent window positioned distally of the receiving fiber optic. In the illustrated embodiment, two transmitting surfaces 47 and two receiving surfaces 49 are provided each communicating with the spectrometer 37 via a unique communication line 34.

Transmission and reception of, for example, visible light, can alternatively be accomplished though a single transparent window, and embodiments in which the transmission and reception signals are propagated through the same fiber optic or through closely adjacent fiber optics are also contemplated. Propagation of transmission and reception signals through the same fiber optic can be accomplished such as by the provision of a coupler at the proximal end to split the transmission and reception signals for processing at detector 37 as will be understood in, among others, the blood oximetry detector arts. Alternatively, one or more separate transmit surfaces 47 and receiving surfaces 49 may be provided, and anywhere within the range of from about 1 to about 12 of each transmit surface 47 and receiving surface 49 may be provided as desired.

Signal transmitting bundle 35 thus provides communication between the transmit surface 47 and receiving surface 49, and a detector 37 such as a spectrometer which remains outside of the patient. The construction and use of spectrometers such as to measure RGB and other UV, visible and IR wavelengths is well understood in the pulse oximetry art, among others, and will not be disclosed in detail herein. In general, transmitter/detector 37 is able to transmit multiple wavelengths of light, which propagate beyond the transmit surface 47 and into a target beyond the distal end 24 of the dilator 20. Some of the transmitted light is absorbed in the target, while other transmitted light is reflected back and received at receiving surface 49. The reflected light is thereafter propagated to the light detector 37 for processing. The present inventors have determined that the light detector 37 in combination with the dilator of the present invention can identify when the distal end 24 of the dilator 20 is positioned against the fossa ovalis of the intraatrial septum, as opposed to other portions of the septum or muscle wall, due to the unique characteristics of light observed at the fossa ovalis.

Depending upon the characteristics of the transmitted light, reflected light at the fossa ovalis will exhibit unique characteristics imparted by (1) light reflected at the surface of or within the fossa ovalis, (2) light reflected through the fossa ovalis by blood in the left atrium, or (3) a combination of the foregoing. The ability of an optical detector to locate the fossa based upon light propagated through the fossa is based upon several circumstances. The blood in the right atrium is relatively poorly oxygenated, and therefore more blue than red. The left atrium contains well oxygenated blood which tends to be relatively red. The fossa is thin enough to allow light to be transmitted across the fossa and into and from the left atrium while the fossa locator is still on the right atrial side. All other areas of the septum are generally thick enough that they will not allow significant light transmission between the right atrium and the left atrium. Thus, in an embodiment of the invention which utilizes light transmission through the fossa, the location of relatively red blood indicates transmission into the left atrium which will generally only happen at the fossa.

Alternatively, the septum contains oxygenated blood and therefore has a certain level of red transmission. The fossa, however, is a thin translucent membrane which is almost yellow. Non-oxygenated blood within the right atrium is relatively blue, while oxygenated blood within the left atrium is red. Location of the fossa may thus alternatively be accomplished by identifying the presence of a translucent, near yellow membrane. The use of multiple wavelengths, transmission, and detectors will allow assessment of both the near yellow color of the fossa, as well as the red color identified through the fossa as will be apparent to those of skill in the art in view of the disclosure herein.

The method of the present invention may additionally be accomplished by providing a light source within the left atrium. The left atrium light source may be provided on any of a variety of left atrium access catheters, as will be apparent to those of skill in the art. Light generated in the left atrium, will be detectable in the right atrium either exclusively at the fossa, or with a greatest intensity appearing at the fossa. Thus, the left atrium dilator 20 need only be provided with light detector optics and electronics, to identify the fossa based upon the characteristics of light received from the right atrium light source.

The dilator 20 is additionally provided with a tissue piercing structure 42 such as a needle 44. Needle 44 preferably comprises a tubular structure such as a stainless steel hypotube having a sharpened distal end 50. The sharpened distal end 50 of needle 44 is axially moveable advanceable through an aperture 45 in the distal end 24 of the tubular body 26.

In one embodiment of the invention, the needle 44 has an axial length of from about 1 cm to about 5 cm, an inside diameter of about 0.022 inches and an outside diameter of about 0.032 inches. Any of a variety of other dimensions for needle 44 may also be used depending upon the desired performance and overall catheter dimensions. Needle 44 is connected to the distal end 40 of a control element such as core wire 36 which axially moveably extends throughout the length of tubular body 26. The proximal end 38 of the core wire 36 in the illustrated embodiment extends proximally from the core wire port 32. The needle 44 is preferably axially moveable between a first position in which the tip 50 is contained within the distal end 24 of the tubular body 26 and a distal position in which the distal tip 50 of the needle 44 is exposed beyond the distal end of the body 26 such as for piercing the fossa ovalis. Distal advancement of the proximal end 38 of core wire 36 will advance the needle 44 from the first position to the second position as will be appreciated in view of the disclosure herein. Alternatively, the needle 44 and core wire 36 may be removed entirely from the dilator 20 except when desired to pierce the septum.

The proximal end 38 of the core wire may be exposed beyond the proximal end of core wire port 32 as in the illustrated embodiment, such that the physician can grasp the core wire 36 and advance it distally with optimum tactile feedback. Alternatively, the proximal end 38 of core wire 36 may be connected to any of a wide variety of controls such as a slider switch, rotatable knob or other control attached to or adjacent the manifold 28. Manipulation of the control can controllably reciprocally move the needle 44 between the first and second position.

In an alternate embodiment, disclosed in FIGS. 6–10, the needle 44 removably extends throughout the entire length of the dilator 20. For this embodiment, needle 44 may have an axial length of from about 100 cm to about 120 cm or longer, and, in one embodiment, about 110 cm.

In the illustrated embodiment, radiopaque dye can be injected through the central lumen 39, and through the hollow needle 44 (if present) for assessing the position of the distal end 24 of the dilator 20. Alternatively, blood may be withdrawn and analyzed for $O_2$ content by well known methods. Left atrial blood will have an $O_2$ saturation of greater than 90%, whereas right atrial blood has an $O_2$ saturation of less than 80%. A separate injection lumen (not illustrated) can be readily provided if desired for a particular application. In addition, the needle 44 may be removable from the dilator 20. In this construction, the dilator 20 retains its greatest flexibility such as for advancement into the intraatrial access site. Once the distal end 24 of the dilator 20 is positioned within the left atrium, the piercing structure 42 such as needle 44 can be loaded into the proximal end 22 of the dilator 20 and advance distally throughout the length of the dilator 20 and out a distal aperture 45. Once the piercing structure 42 has pierced the fossa ovalis or other structure, and the distal end 24 of the dilator 20 is advanced through the opening formed by the piercing structure, the piercing structure 42 may be proximally retracted and removed from the dilator, thereby leaving the central lumen fully available for subsequent therapeutic or diagnostic devices or materials.

Figure 21:
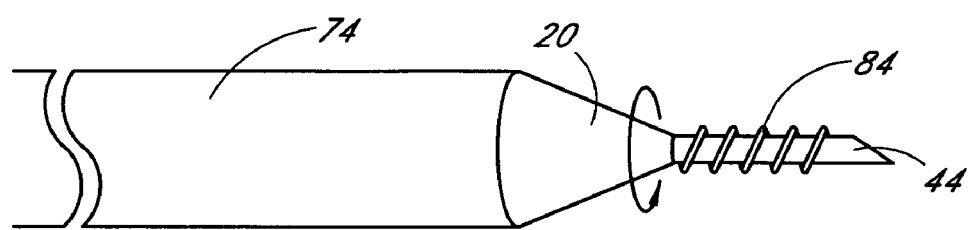
FIG. 21 is a side view of the needle in accordance with one embodiment of the present invention.
Figure 22A:
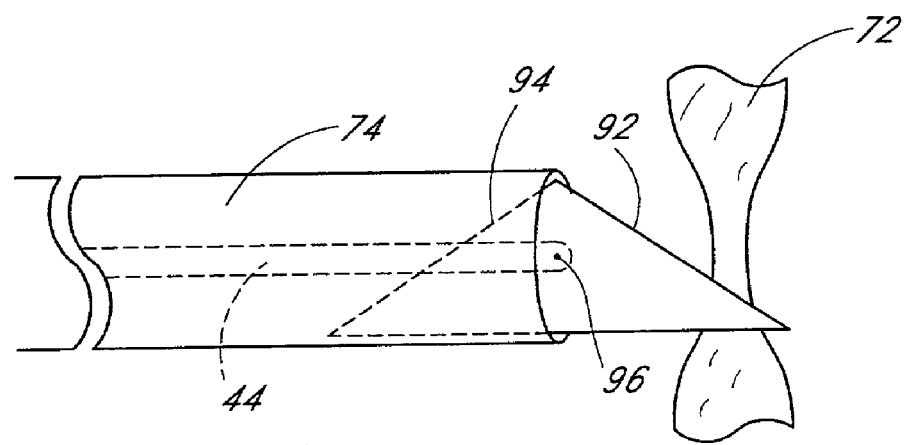
FIGS. 22A–22H are side views of various needles in accordance with further embodiments of the present invention.
Figure 22B:
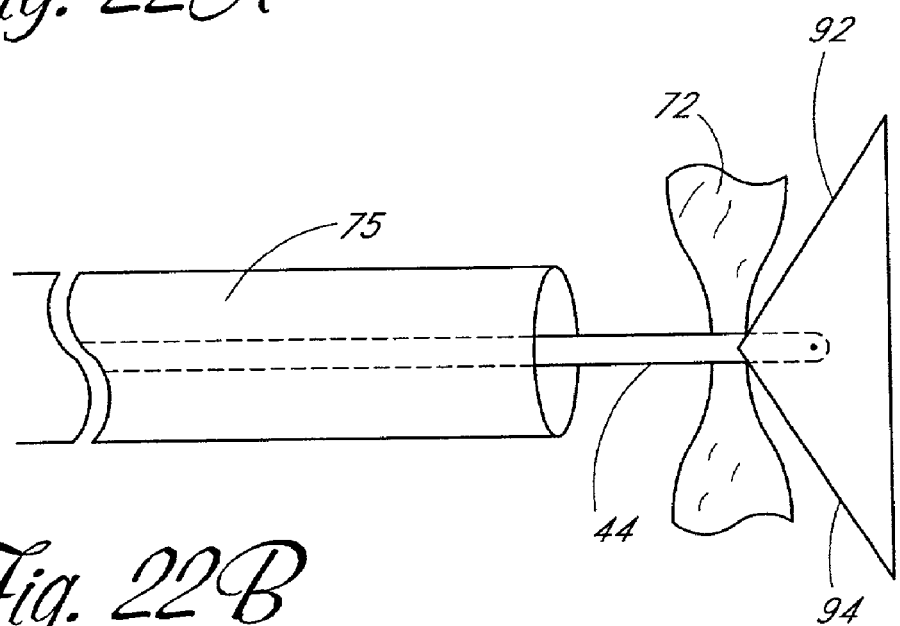

In one embodiment, illustrated in FIG. 21, the needle 44 may be provided with a corkscrew thread or other helical structure 84, such as those having substantially circular or triangular cross-sections, thereby permitting the needle 44 to penetrate the fossa ovalis 72 by rotating while moving transversely through the opening. One of ordinary skill in the art will appreciate that the size, shape and orientation of the helical structures can be adjusted depending on the desired combination of minimizing resistance during puncture or increasing the size opening.

Where it is desirable to increase the size of the opening created by the needle 44, the needle may be configured to create an opening when advanced in the distal direction, and to enlarge the opening when advanced back through the fossa ovalis in the proximal direction. This may be accomplished by providing additional cutting means, such as edges, on the needle 44. In one embodiment, illustrated in FIG. 22a, the needle has a primary cutting edge 92 that is rotatably attached to the distal end of the needle 96. The primary cutting edge 92 punctures the fossa ovalis 72 when the needle 44 is advanced in the distal direction. The distal end of the needle 44 is advanced into the left atrium and the primary cutting edge 92 is rotated in the left atrium to expose one or more additional cutting surface 94, such as by means of an axially moveable pull-wire as disclosed elsewhere herein, or by other appropriate remote control or biasing means as are well known to those ordinary skill in the art. Retracting the needle back through the fossa ovalis 72 in the proximal direction with the additional cutting surface 94 in the exposed configuration, as illustrated in FIG. 22b, results in a larger opening in the fossa ovalis 72.

Figure 22C:
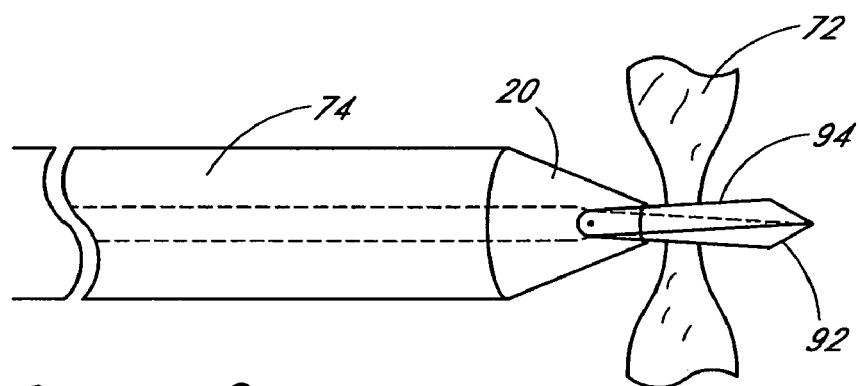
Figure 22D:
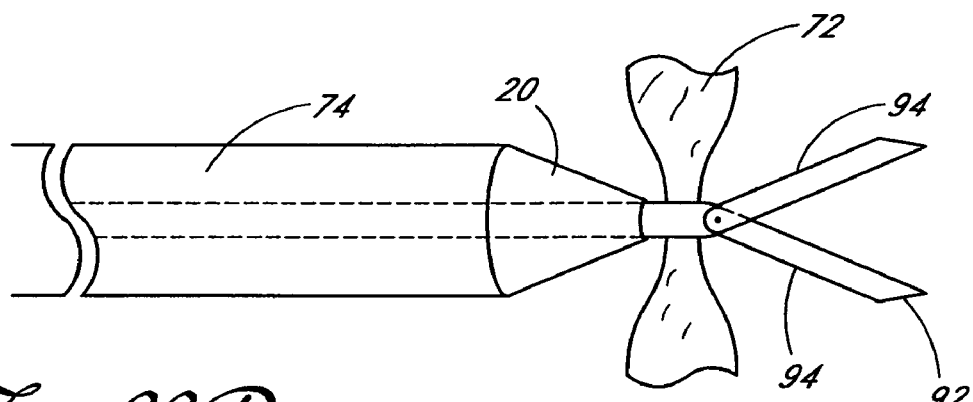

In another embodiment, illustrated in FIG. 22c, the needle 44 has two or more primary cutting edges 92 that are attached to the needle 44 in a scissors-like configuration. The primary cutting edges 92 puncture the fossa ovalis when the needle 44 is advanced in the distal direction. The primary cutting edges 92 can be opened in the left atrium to expose one or more additional cutting surfaces 94, such as by means of an axially moveable pull-wire as disclosed elsewhere herein, or by other appropriate remote control or biasing means as are well known to those ordinary skill in the art. Retracting the needle back through the fossa ovalis 72 in the proximal direction with the additional cutting surfaces 94 in the exposed configuration, as illustrated in FIG. 22d, results in a larger opening in the fossa ovalis 72.

Figure 22E:
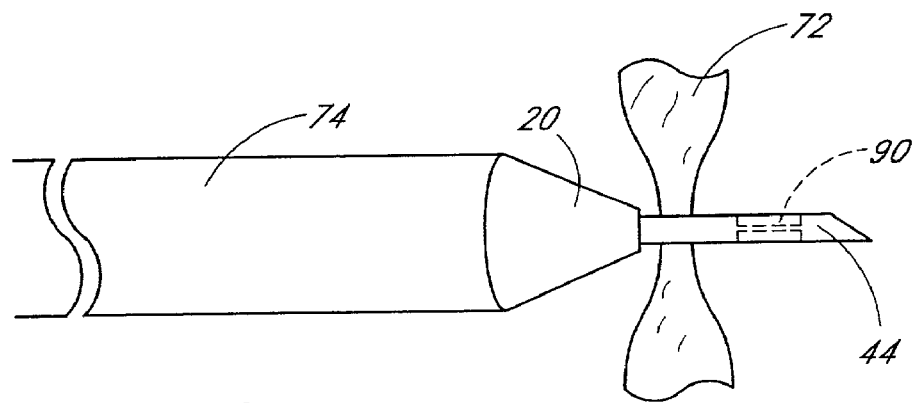
Figure 22F:
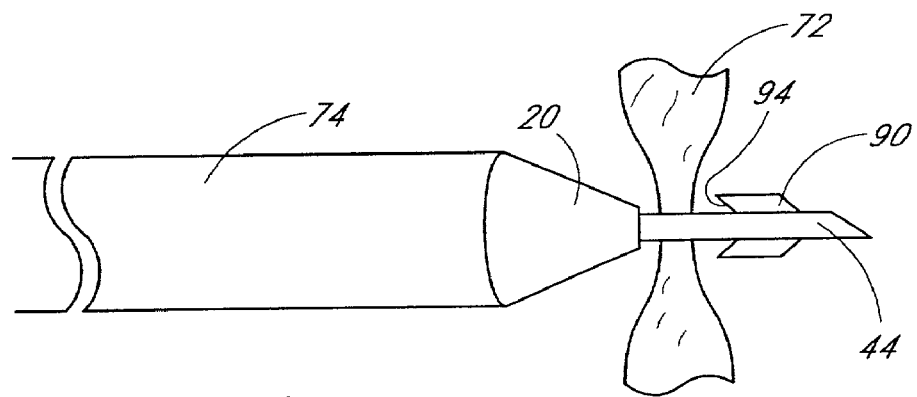
Figure 22G:
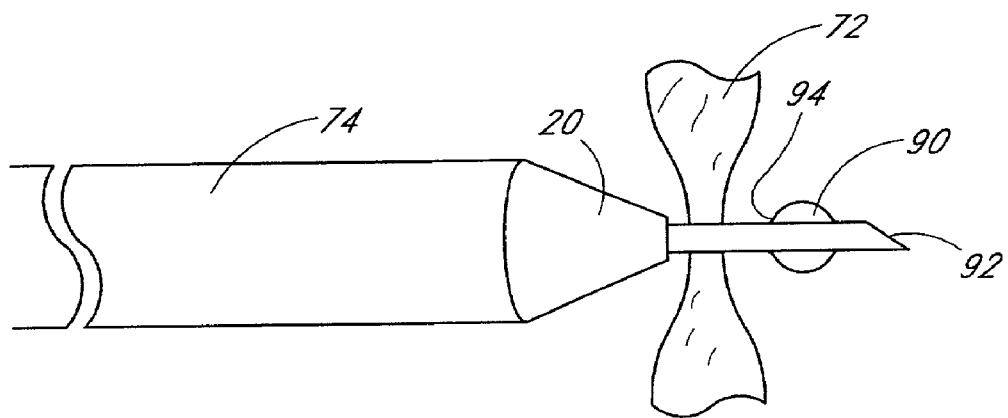

In another embodiment, illustrated in FIG. 22e, the needle 44 has two or more wings 90 that are contained within the needle 44 when the needle 44 is advanced in the distal direction. The wings 90 are optionally biased to expand when the needle 44 has crossed the fossa ovalis. Alternatively, the wings 90 are expanded from the proximal end of the needle 44 such as by means of an axially moveable pull-wire as disclosed elsewhere herein, or by other appropriate remote control or biasing means as are well known to those ordinary skill in the art. As illustrated in FIGS. 22f and 22g, expanding the wings 90 exposes secondary cutting surfaces 94. Retracting the needle back through the fossa ovalis 72 in the proximal direction with the additional cutting surfaces 94 in the exposed configuration results in a larger opening in the fossa ovalis 72.

Figure 22H:
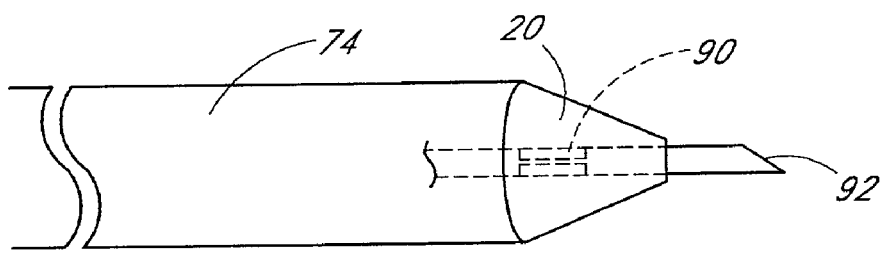

As illustrated in FIG. 22f, the wings 90 may be configured with secondary cutting surfaces 94 inclined at an angle extending toward the proximal end of the needle. Alternatively, as illustrated in FIG. 22g, the wings 90 may be configured with rounded secondary cutting surfaces 94. The wings 90 may also be inclined at an angle extending toward the distal end of the needle or at an angle perpendicular to the axis of the needle. As illustrated in FIG. 22H, in those embodiments where the secondary cutting surfaces 94 are rounded or inclined at an angle extending toward the distal end of the needle, the wings 90 may be withdrawn back into the needle 44 by advancing the needle 44 distally into the dilator 20.

Although certain embodiments incorporating secondary cutting surfaces have been illustrated in conjunction with a dilator 20 as disclosed herein, one of ordinary skill in the art will appreciate that secondary cutting surfaces can be used with, or without, a dilator 20. The optimal type of dilator, if any, to use with a needle having one or more secondary cutting surfaces will depend on the particular application as well as the design of the primary and secondary cutting surfaces, and can be determined though routine experimentation.

In general, the cutting surfaces or other dilatation surfaces are advanceable from a first, reduced crossing profile for advancement in a first direction (e.g., distally through the fossa ovalis), and a second, enlarged crossing profile for movement in a second direction (e.g., proximal retraction back through the fossa ovalis). Any of a variety of structures can be utilized, in which the cutting surface or tissue engagement surface is moveable from a first orientation in which it extend generally parallel to the longitudinal axis of the needle or other catheter component for penetration through a tissue surface, and a second, inclined orientation with respect to the longitudinal axis to present a larger cross sectional area. Such structures may be biased in the direction of the second, enlarged crossing profile and restrained by a movable sheath, pull wire or other retention structure. Alternatively, the tissue engagement surface may be neutrally biased, and moved between the reduced crossing profile and enlarged crossing profile orientations by axial movement of a pull wire. As a further alternative, such structures may be advanced into the enlarged crossing profile by inflation of an underlying balloon in communication with the proximal end of the catheter by an axially extending inflation lumen.

Figure 16A:
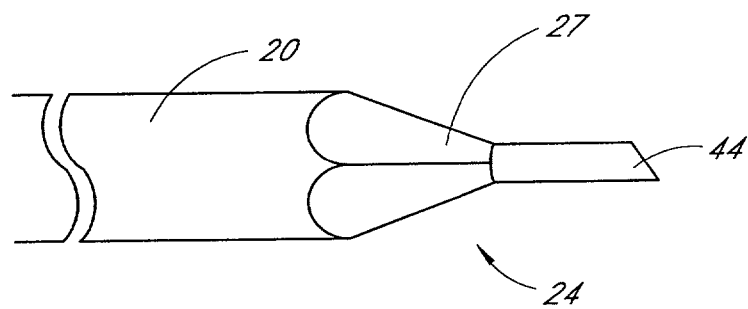
FIGS. 16A–C are side views of various dilators in accordance with further embodiments of the present invention.
Figure 16B:
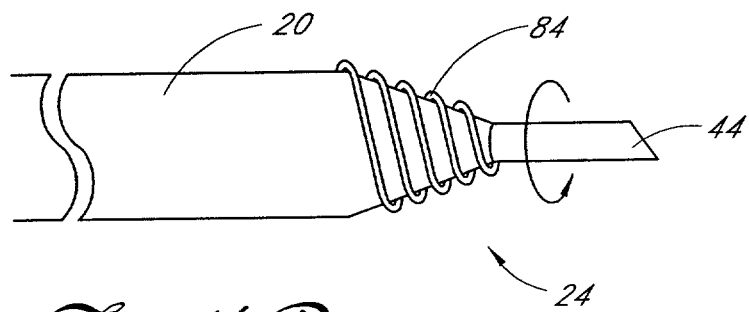
Figure 16C:
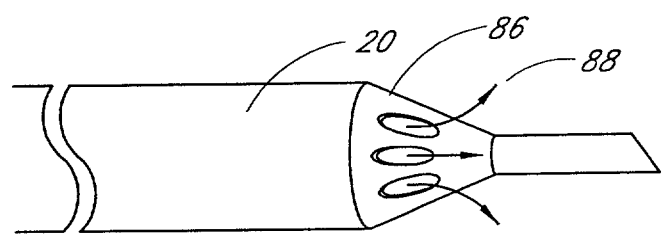

As illustrated in FIG. 16A, the distal end 24 of dilator 20 is provided with a tapered frustro conical surface 27. This allows the tubular body 26 to function as a dilator, thereby permitting the tapered surface 27 to enlarge the opening formed by needle 44 while minimizing "tenting" of the fossa ovalis during the transseptal access procedure. Alternatively, as illustrated in FIG. 16b, the distal end 24 of dilator 20 may be provided with a corkscrew or other helical structure 84, such as those having threads with semi-circular or triangular cross-sections, thereby permitting the dilator to enlarge the opening formed by needle 44 by rotating while moving transversely through the opening. In yet another embodiment, illustrated in FIG. 16c, the distal end 24 of dilator 20 may be provided with one or more nozzles 86 capable of generating a high-pressure stream 88 of fluid, such as saline solution, thereby enlarging the opening formed by needle 44. Optionally, in all of these embodiments, the dilator 20 may be transversely advanced while the dilator 20 is spinning or rotating with respect to the fossa ovalis.

Various embodiments of the present invention have been disclosed wherein the needle 44 and dilator 20 have been described as separate structures. One of ordinary skill in the art will recognize that the needle and dilator need not be physically separate structures and will appreciate that the allocation of particular features to the needle or dilator is illustrative only. For any particular application, the optimal allocation of the features disclosed herein as part of a single physical structure or physically part of either the needle or dilator will be apparent to one or ordinary skill in the through routine experimentation.

In accordance with the method of the present invention, the right atrium may be initially accessed with a transseptal access system through either the inferior or superior vena cava, which initially requires cannulation with an introducer sheath such as through the well known "Seldinger" technique. The transseptal access system of the present invention includes a transseptal sheath, a piercing dilator catheter 20 as discussed above, and an appropriately sized guidewire.

Figure 12:
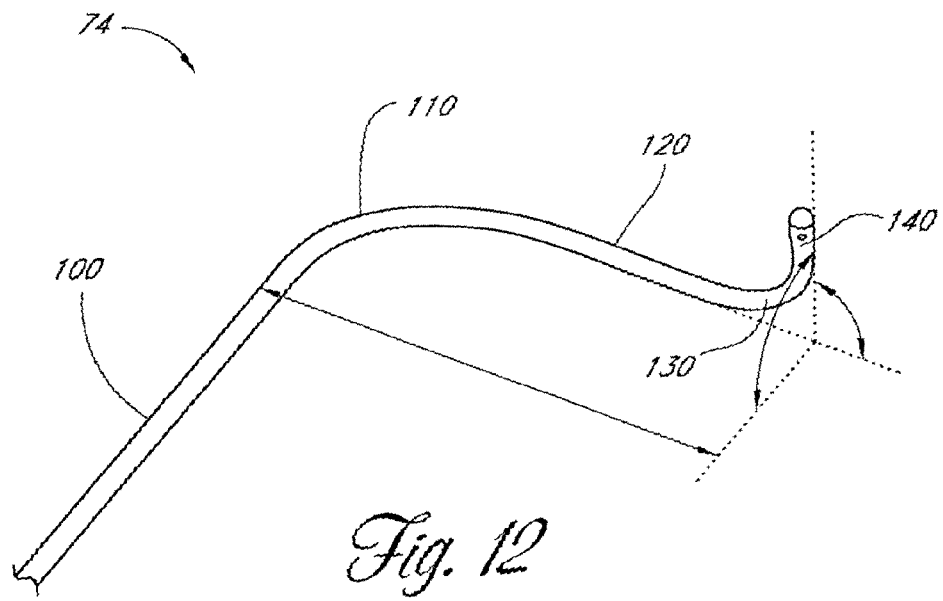
FIGS. 12 and 13 are perspective schematic views of a transseptal access sheath in accordance with the present invention.

Illustrated in FIG. 12 is an embodiment of an access sheath 74. In general, the sheath 74 comprises an elongate, flexible tubular body having preset bends as described below. In an unstressed configuration the sheath 74 comprises a first substantially linear section 100, a first curved section 110 and a second curved section 130. As used herein, the term substantially linear also encompasses structures that are actually linear. The first curved section 110 is distal to the first substantially linear section 100, and the second curved section 130 is distal to the first curved section 110. Preferably, there is a second substantially linear section 120 between the first and second curved sections, and a third substantially linear section 140 distal to the second curved section. In other embodiments the first curved section 110 transitions directly into the second curved section 130 so there is no second substantially linear section 120, and in other embodiments there is no third substantially linear section 140 distal to the second curved section.

In one embodiment, the sheath is designed to facilitate access to the left atrium. In other embodiments, the sheath is designed to facilitate access to other physiological structures, such as the LAA, the orifice of the LAA, the distal aspect of the LAA, or pulmonary vein such as the left superior pulmonary vein. One of ordinary skill in the art can determine the optimum geometric orientation of the sheath for any particular application based on the desired region of access and the particular patient's physiology through routine experimentation in view of the disclosure herein. In one embodiment that is useful for accessing regions of the LAA, the first curved section is shaped to abut the interior wall of the right atrium substantially opposite the fossa ovalis while directing the distal tip toward the fossa ovalis. This facilitates location of the fossa ovalis through tactile or other sensing means as described herein. The second curved section is shaped to facilitate location and access of the desired region of the LAA after penetration of the fossa ovalis. One of ordinary skill in the art will recognize that the precise shape of these curves will depend on the patient's physiology and can be determined through routine experimentation.

The first and second curved sections may be provided in accordance with any of a variety of techniques. For example, the first and second curved sections may be introduced prior to insertion of the sheath into the body by bending the sheath, such as around a forming mandrel under heat or in excess of the elastic limit of the sheath. Alternatively, an injection molded sheath body may be provided with a predetermined bend, or by heat setting such as with removable flexible mandrels extending through any interior lumen to maintain patency of the lumen around the bend. Alternatively, the first and second curved sections may be formed during or after placement of the sheath in the patient. This may be accomplished by providing the sheath with any of a variety of steering mechanisms, which allow a distal portion of the sheath to be inclined away from the axis of the normal bias of the catheter. For example, one or more axially moveable pull wires may extend through the length of the sheath. Proximal traction on a pull wire that is secured at a distal location of the catheter will cause a lateral defection of the catheter. Other techniques will be known to those of skill in the art.

The geometric orientation of certain preferred embodiments that are useful for accessing regions of the LAA are described below. As will be appreciated by one of ordinary skill in the art, depending on the patient's physiology and the location to which access is sought, the objects of the invention can be achieved by varying the geometric design of the sheath without departing from spirit of the invention. In particular the invention contemplates adding additional curved sections and/or by adding additional substantially linear sections.

Figure 13:
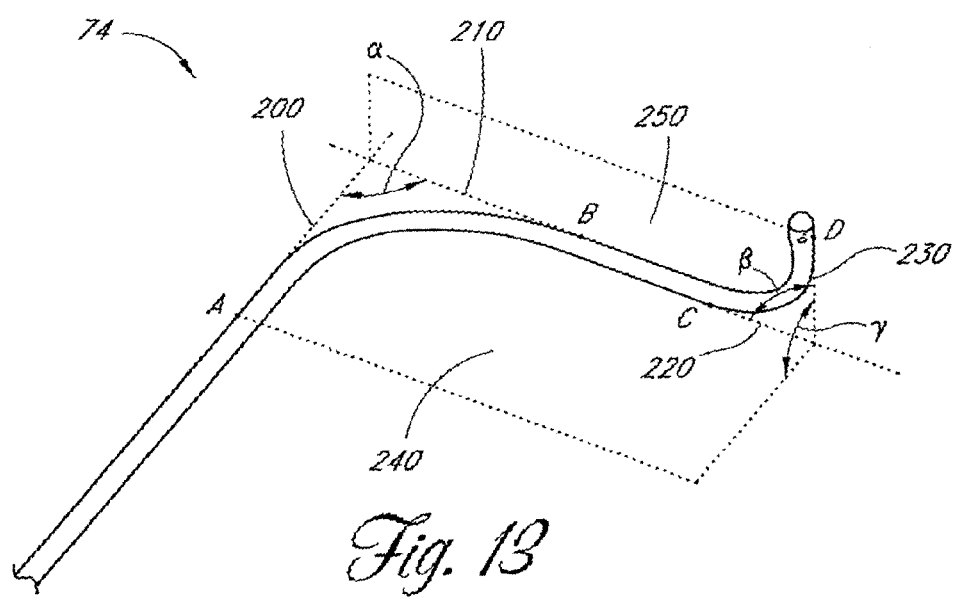

In one embodiment, illustrated in FIG. 13, the point where the first substantially linear section 100 begins to transition into the first curved section 110 defines a first proximal edge point A on the outside edge of the exterior of the sheath. A tangent 200 to the outer edge of the first curved section 110 at the first proximal edge point A is substantially parallel to the first substantially linear section 100. The point where the first curved section 110 begins to transition into the second substantially linear section 120 defines a first distal edge point B on the outside edge of the exterior of the sheath. A tangent 210 to the outer edge of the first curved section 110 at the first distal edge point B is substantially parallel to the second substantially linear section 120. In those embodiments where there is no second substantially linear section 120 or where there are additional curved or substantially linear sections, the first distal edge point B is defined as the first inflection point distal to the first curved section 110 on the outside edge of the exterior of the sheath. A tangent 210 to the outer edge of the first curved section 110 at the first distal edge point B is substantially parallel to the outside edge of the exterior of the sheath at point B.

The point where the second substantially linear section 120 begins to transition into the second curved section 130 defines a second proximal edge point C on the outside edge of the exterior of the sheath. A tangent 220 to the outer edge of the second curved section 130 at the second proximal edge point C is substantially parallel to the second substantially linear section 120. In those embodiments where there is no second substantially linear section 120 or where there are additional curved or substantially linear sections, the second proximal edge point C is defined as the first inflection point proximal to the second curved section 130. A tangent 220 to the outer edge of the second curved section 130 at the second proximal edge point C is substantially parallel to the outside edge of the exterior of the sheath at point C.

The point where the second curved section 130 begins to transition into the third substantially linear section 140 defines a second distal edge point D on the outside edge of the exterior of the sheath. A tangent 230 to the outer edge of the second curved section 130 at the second distal edge point D is substantially parallel to the third substantially linear section 140. In those embodiments where there is no third substantially linear section 140 the second distal edge point D is defined as the distal end point of the outside edge of the exterior of the sheath. In those embodiments where there are additional curved or substantially linear sections distal to the second curved section 140 the second distal edge point D is defined as the first inflection point distal to the second curved section 130. A tangent 220 to the outer edge of the second curved section 130 at the first distal edge point B is substantially parallel to the outside edge of the exterior of the sheath at point B.

The tangent 200 and the tangent 210 intersect to form an angle $\alpha$. The angle $\alpha$ is preferably about 90 degrees, generally between about 75 degrees and about 105 degrees, and in other embodiments may be in the range of about 80 degrees to about 100 degrees. The tangent 220 and the tangent 230 intersect to form an angle $\beta$. The angle $\beta$ is preferably about 90 degrees, generally between about 75 degrees and about 105 degrees, and in other embodiments may be in the range of about 80 degrees to about 100 degrees. The tangent 200 and the tangent 210 also define a plane, 240. The tangent 220 and the tangent 230 also define a plane, 250. The plane 240 and the plane 250 define an angle $\gamma$. The angle $\gamma$ is preferably about 90 degrees, generally between about 75 degrees and about 105 degrees and in other embodiments may be in the range of about 80 degrees to about 100 degrees.

The first curved section 110 has an arc length along the outside edge of the exterior of the sheath between point A and point B in the range of about 7.5 cm to about 9.5 cm. The second curved section 120 has an arc length along the outside edge of the exterior of the sheath between point C and point D in the range of about 5 cm to about 7.5 cm.

The sheath also defines a Cartesian coordinate system. The origin of this coordinate system is defined as point A. The X-axis is defined as parallel to tangent 200. The Y-axis is defined as the normal to tangent 200 in plane 240. The Z-axis is defined as the normal to plane 240 at point A. In one embodiment, the distance along the Y-axis between point A and point D is about 9 cm. In other embodiments, one of ordinary skill in the art will appreciate that the distance may vary depending upon the patient's physiology, for example within the range of about 6 cm to about 15 cm. In one embodiment, the distance along the Z-axis between point C and point D is about 3.5 cm. In other embodiments, one of ordinary skill in the art will appreciate that the distance may vary depending upon the patient's physiology, for example within the range of about 1 cm to about 6 cm.

In one embodiment, the first curved section 110 has a radius of curvature of about 5 cm. In other embodiments, one of ordinary skill in the art will appreciate that the radius of curvature may vary depending upon the patient's physiology, for example within the range of about 3 cm to about 10 cm. In one embodiment, the second curved section 130 has a radius of curvature of about 3 cm. In other embodiments, one of ordinary skill in the art will appreciate that the radius of curvature may vary depending upon the patient's physiology, for example within the range of about 1 cm to about 6 cm.

Preferably the sheath is sufficiently tourqueable that the location of the distal tip of the sheath can be controlled from the proximal end of the sheath. In one embodiment additional torquability is supplied by re-enforcing the shaft with stainless steel or high strength thin polymeric braid. It is desirable to maximize the lubricity of the inner surface of the sheath to facilitate insertion and removal of various diagnostic and treatment devices within the sheath. In one embodiment the inner surface of the sheath is coated with lubricity enhancing material, such as PTFE.

Manageability and atraumaticity are facilitated by varying the stiffness of the sheath along its length. It is desirable for the proximal section of the sheath to be relatively more stiff for torquability and kink resistance, and for the distal section of the sheath to be relatively less stiff. Generally, it is advantageous to soften the material comprising the sheath, and/or to make the wall of the sheath thinner toward the distal end. In one embodiment, the proximal section of the sheath comprises 70D Pebax and has a wall thickness of about 0.015 inches, the intermediate section of the sheath comprises 40D Pebax and has a wall thickness of about 0.015 inches, and the distal section of the sheath comprises 40D Pebax and has a wall thickness of about 0.011 inches. In one embodiment, the proximal section of the sheath extends for about 55 cm, the intermediate section of the sheath extends for about 13 cm, and the distal section of the sheath extends for about 2 cm. In other embodiments, the proximal section of the sheath may extend from about 40 cm to about 65 cm, the intermediate section of the sheath may extend from about 5 cm to about 15 cm, and the distal section of the sheath may extend from about 2 mm to about 50 mm.

One of ordinary skill in the art will appreciate that the shaft may be made of a greater or lesser number of sections having varying compositions and durometer hardnesses, that there may be gradual or abrupt transition between the sections, that the various sections may comprise a variety of other materials, and that the thickness of the sheath wall may also be adjusted. The desired combination of these parameters will depend on which parameters are selected and particularly useful combinations of these properties will be apparent to one of ordinary skill in the art through routine testing.

The atraumacity of the transition between the needle, dilator, transition catheter or the like may be enhanced by tapering the outer diameter of the distal tip of the sheath and/or tapering the thickness of the wall of the distal tip of the sheath. Visualization of the sheath can be enhanced by marking the distal tip of the sheath a radiopaque marker. One of ordinary skill in the art will appreciate that the radiopaque marker may be applied as a band, or in other shapes and at varying distances from the distal tip.

Figure 14B:
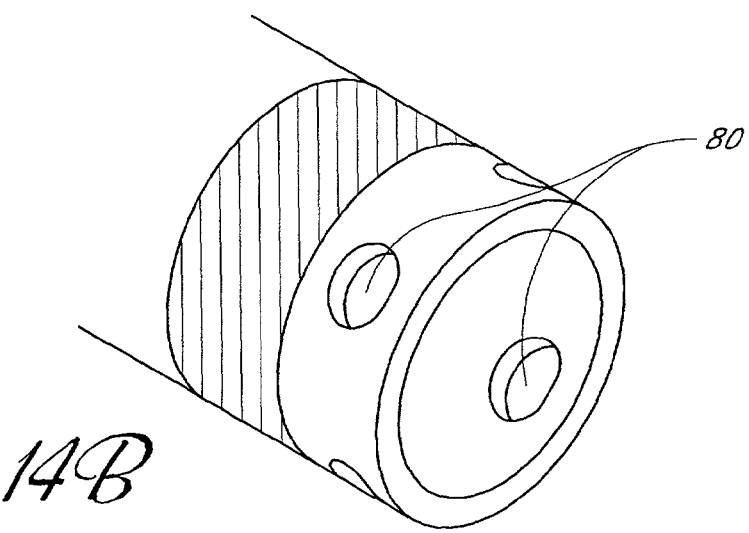
FIGS. 14A–C are perspective views of vents in the transseptal access sheath.
Figure 14C:
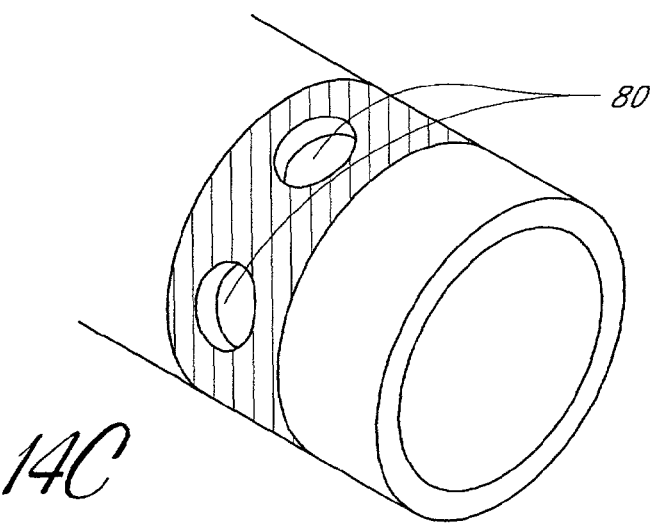
Figure 14A:
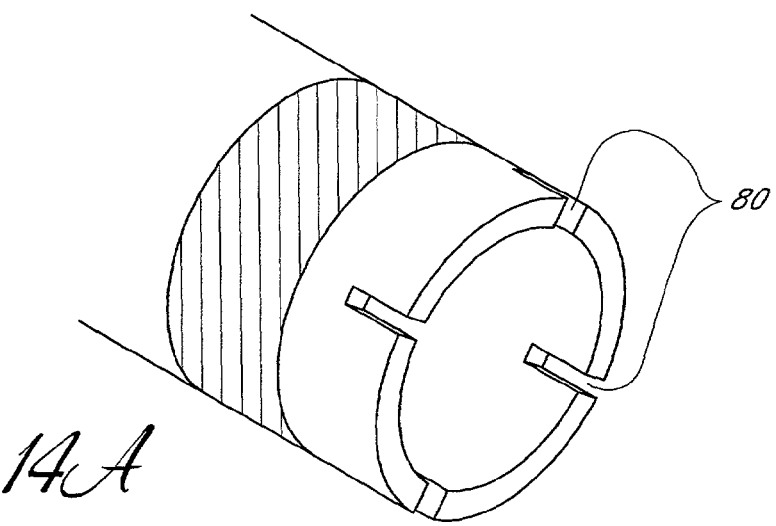

The detrimental effect of drawing air into the catheter can be minimized by providing grooves, vents or holes adjacent the distal end of the sheath. This prevents the creation of a vacuum during the withdrawal of devices from the sheath by allowing blood into the sheath even if the distal opening of the sheath is in sealing contact with tissue. In one embodiment, illustrated in FIG. 14a, the vents 80 are slits in the distal end of the sheath. In another embodiment, illustrated in FIG. 14b, the vents 80 are holes which extend transversely through the wall near the distal end of the sheath. As illustrated in FIG. 14c, the vent holes 80 may also be located within the radiopaque marker band to reduce or prevent collapsing or clogging of the vent holes.

In general, the vents 80 have a diameter or cross sectional area equivalent to a round vent diameter within the range of from about 0.020 inches to about 0.100 inches. Anywhere from about one to about ten or more vents may be provided. In one embodiment, approximately 4 vents, each having a diameter of about 0.040 inches are provided. The vents may be positioned in a single plane transverse to the longitudinal axis of the catheter as illustrated. The vents reside in a plane which is generally no more than about 5 mm from the distal end. Preferably, the vents are positioned within about 3 mm of the distal end of the catheter. Alternatively, the vents may be staggered in two or more transverse planes, depending upon the desired performance characteristics.

In present practice, the preferred access point is along the right femoral vein, although access from the left femoral vein is also possible. Access may also be achieved through a puncture in any of a variety of other veins of suitable internal diameter and the present invention is not limited in this regard.

A conventional spring tipped guide wire is thereafter advanced through the needle into the vein and the needle is subsequently removed. The dilator 20 of the present invention is positioned within a sheath of the type described herein, or other well-known sheaths, such as a 14 French introducer sheath. Subsequently, the sheath and inner dilator 20, in combination with the guide wire, are advanced through the femoral vein to the right atrium.

Referring to FIG. 4, there is illustrated a schematic cross-section of a portion of the heart 60. The right atrium 62 is communication with the inferior vena cava 64 and the superior vena cava 66. The right atrium 62 is separated from the left atrium 68 by the intraatrial septum 70. The fossa ovalis 72 is located on the intraatrial septum 70. As seen in FIG. 4, the sheath 74 having the dilator 20 therein and a guidewire 76 have been positioned within the right atrium 62.

Figure 5:
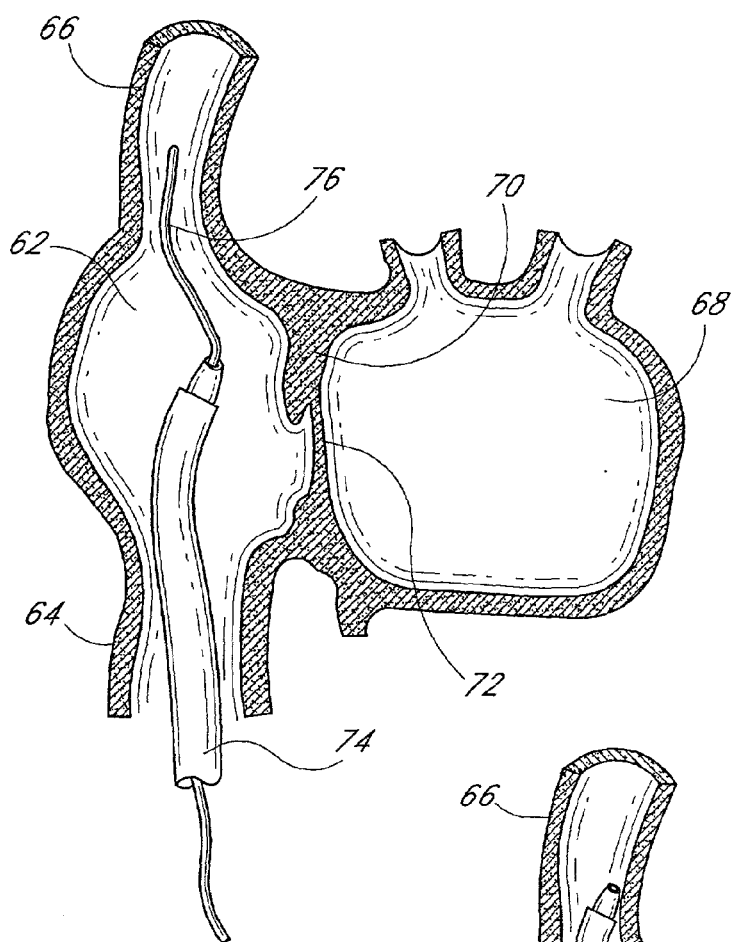
FIG. 5 is a cross-sectional view as in FIG. 4, with the guidewire positioned in the superior vena cava.
Figure 6:
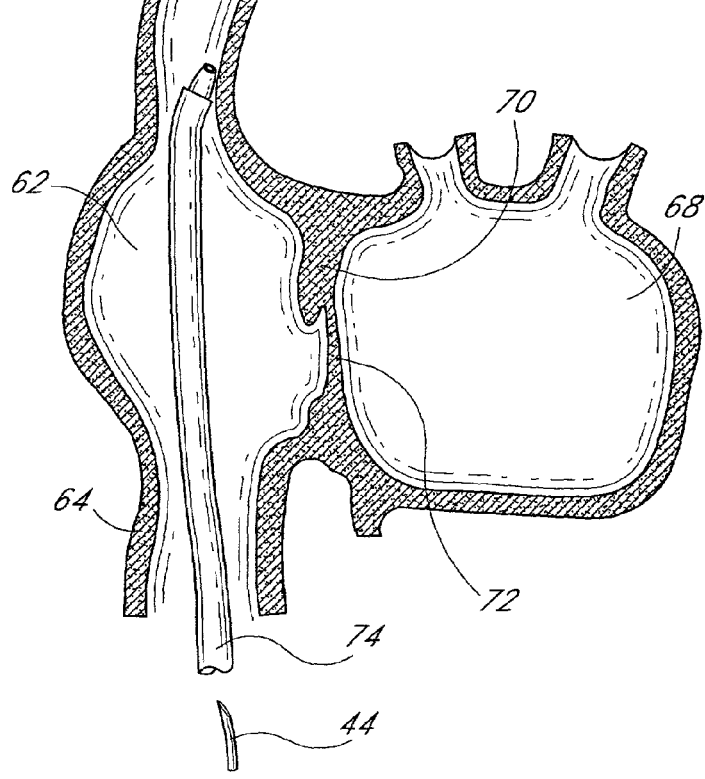
FIG. 6 is a cross-sectional view as in FIG. 4, with the transseptal access catheter positioned against the wall of the superior vena cava.
Figure 7:
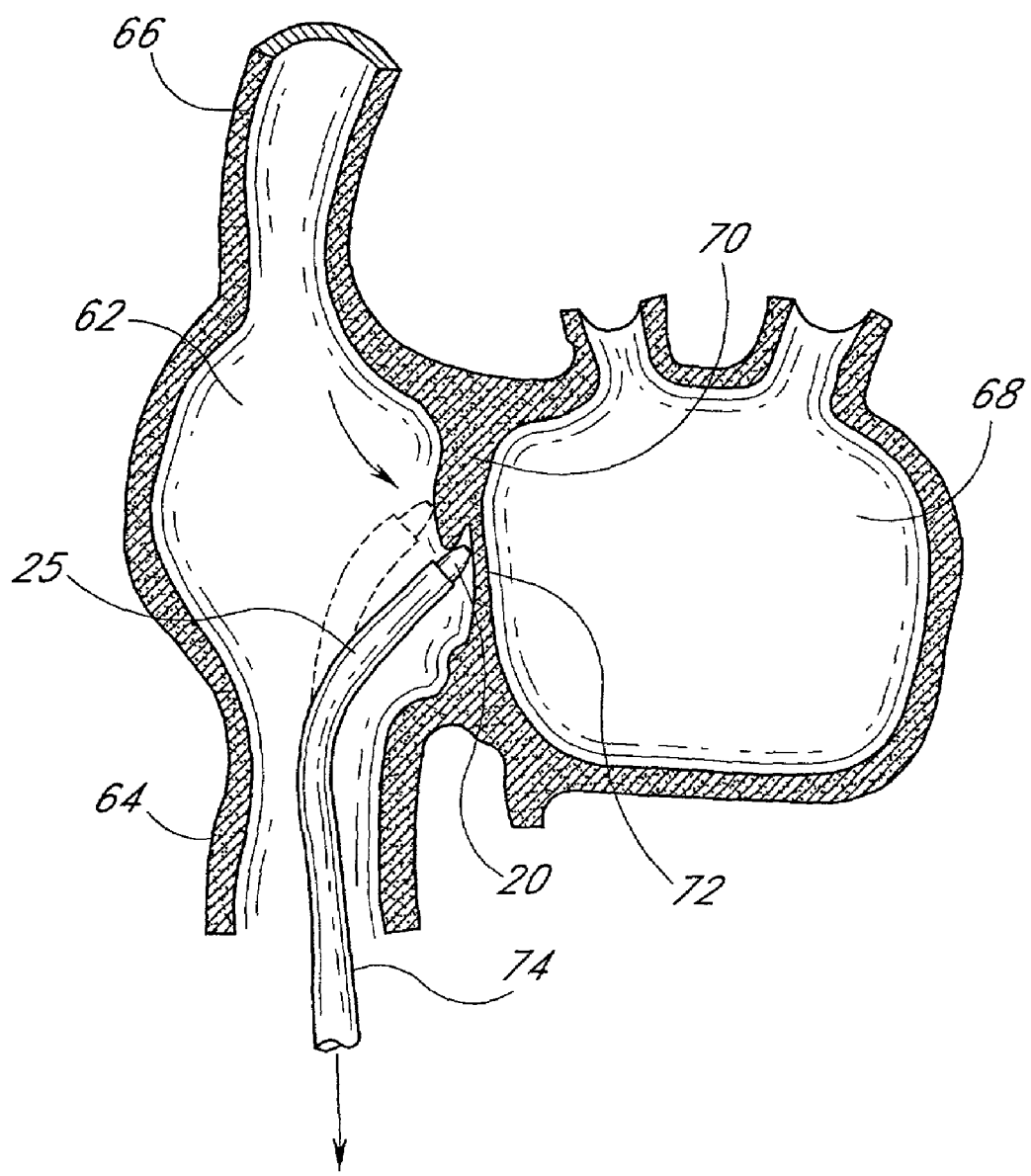
FIG. 7 is a cross-sectional view as in FIG. 4, with the access catheter positioned against the fossa ovalis.
Figure 8:
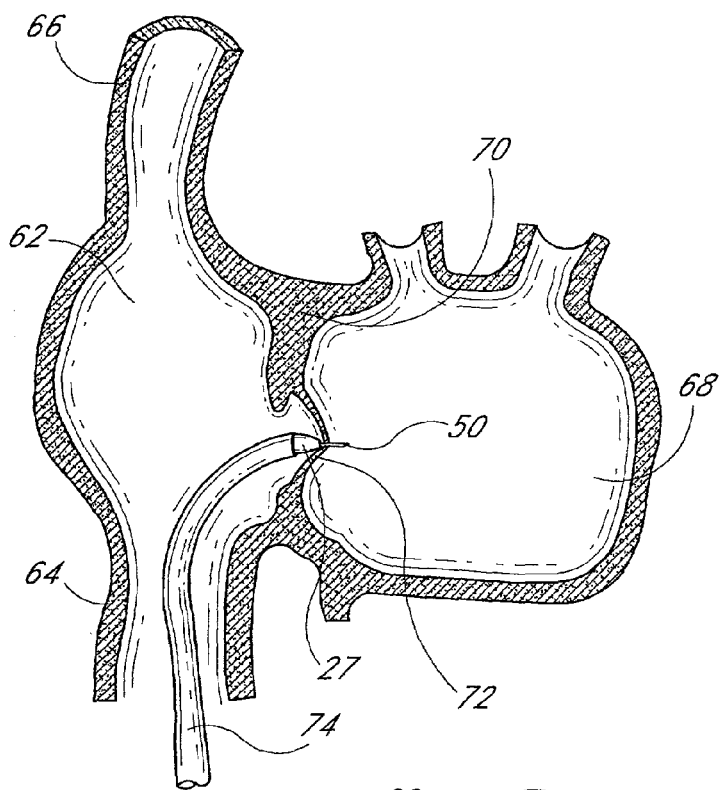
FIG. 8 is a cross-sectional view as in FIG. 4, showing tissue distention or "tenting" as the needle punctures the fossa ovalis.
Figure 9:
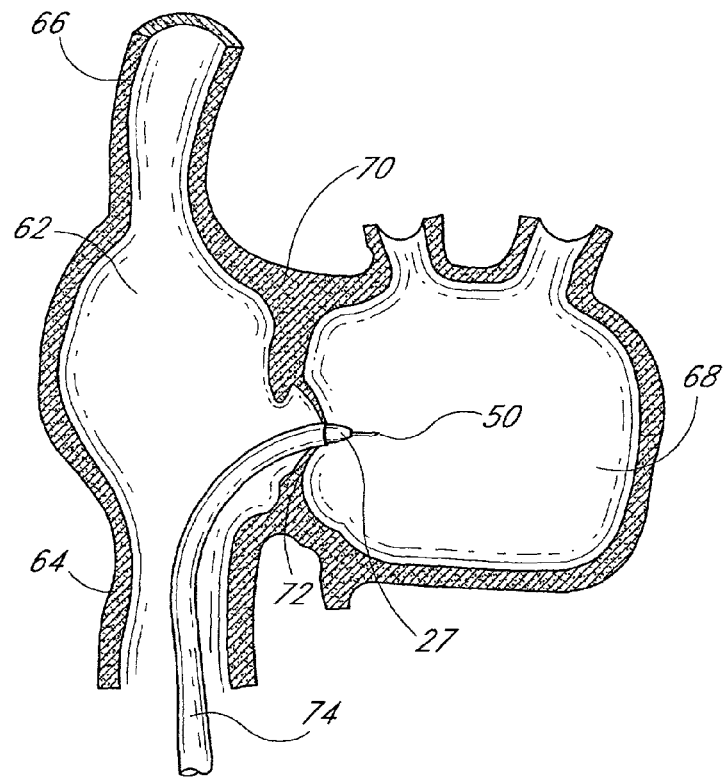
FIG. 9 is a cross-sectional view as in FIG. 8, showing tissue distention as the dilator is advanced through the fossa ovalis.
Figure 10:
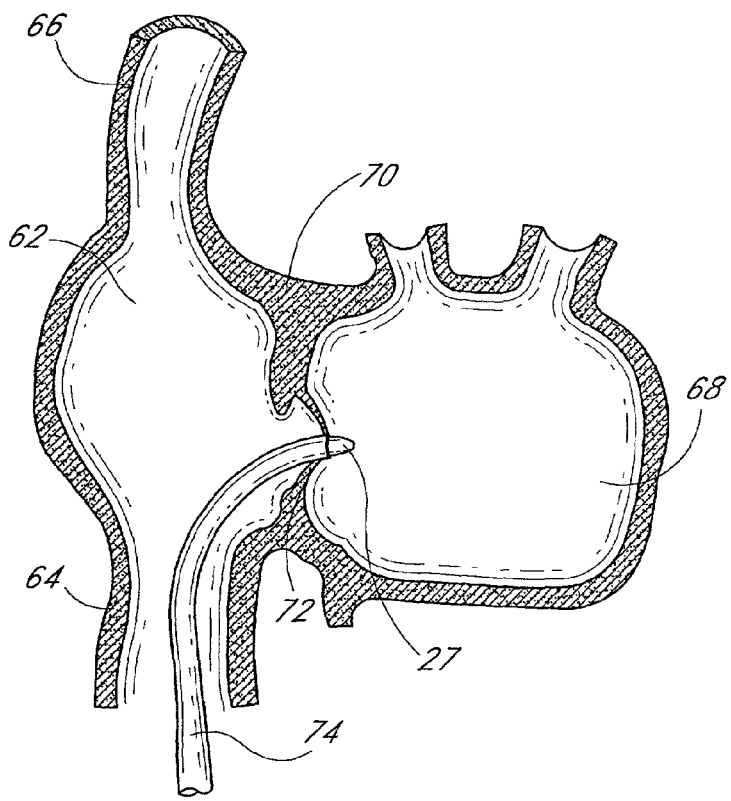
FIG. 10 is a cross-sectional view as in FIG. 9, illustrating the sheath, which has been advanced over the dilator and through the septum.
Figure 11:
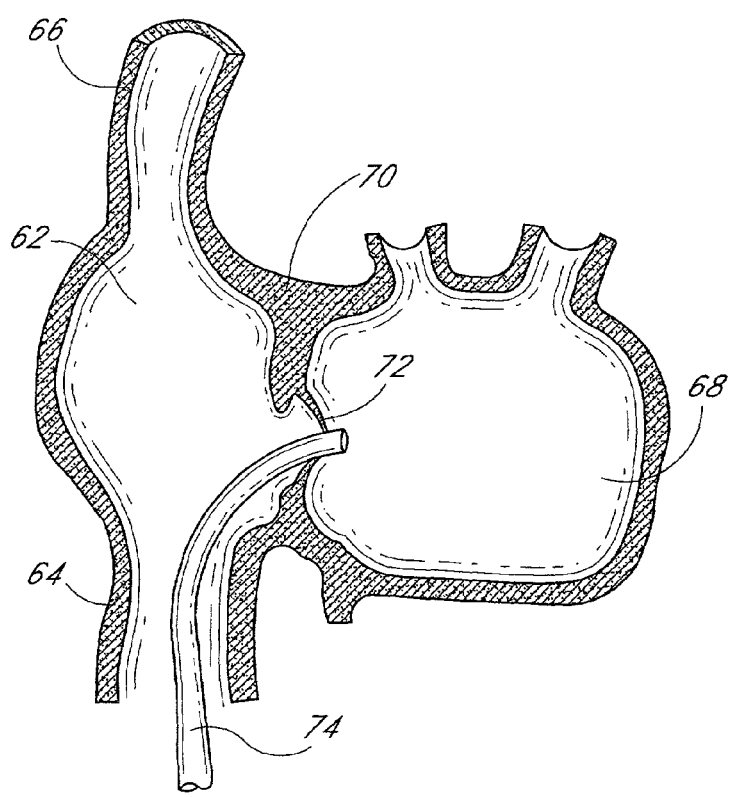
FIG. 11 is a cross-sectional view as in FIG. 10, with the dilator removed, leaving the sheath in place across the fossa ovalis.

The guidewire 76 is thereafter distally advanced to access the superior vena cava 66. See FIG. 5. The dilator 20 and sheath 74 are thereafter advanced into the superior vena cava as illustrated schematically in FIG. 6. The guidewire 76 is proximally retracted.

When the sheath 74 and dilator 20 are in the superior vena cava and the guide wire has been removed, a transseptal needle 44 is advanced through the central lumen 39 of the dilator 20 and sheath 74. The transseptal needle 44 is advanced (possibly with a stylet in place) to a point that the stylet tip is just inside the distal tip of the sheath 74 and dilator 20, a position previously noted by the operator, and the stylet is withdrawn from the transseptal needle.

The remaining combination of the sheath 74 with the dilator 20 having the transseptal needle therein, is then drawn proximally from the superior vena cava while the first curved section 110 of the sheath, alone or in combination with the preset curve 25 at the distal region of dilator 20, causes the tip of the sheath-dilator-transseptal needle combination to "drag" along the wall of the right atrium and the septum 70. Depending upon the particular embodiment of the transseptal access system, some differences in the access method will occur at this point.

For example, in the reflected light embodiment disclosed in connection with FIGS. 1–3, the light source and detector 37 will likely need to be calibrated once the dilator 20 has been placed inside the right atrium 62 but before the tip has been placed against the septum 70. The tip of the dilator 20 is then positioned against the septum 70 by distal advancement through the sheath 74. The tip is then dragged along the septum by proximal traction on the dilator 20 until the tip pops onto the fossa 72. Once the tip is positioned on the fossa 72, the characteristic color at the fossa is detected by the detector 37. A responsive audio or visual signal is generated, confirming that the catheter 20 is now properly positioned at the fossa ovalis 72.

The physician is normally assisted during placement, as in the entire procedure, by fluoroscopy or other visualization techniques. To assist in such visualization, the distal tip of sheath 74 and the distal tip of dilator 20 may be provided with a radiopaque marker. In addition, some physicians find it desirable to infuse a radiopaque dye through the transseptal needle at various stages of the procedure to assist in visualization, particularly following the transseptal puncture.

Figure 20A:
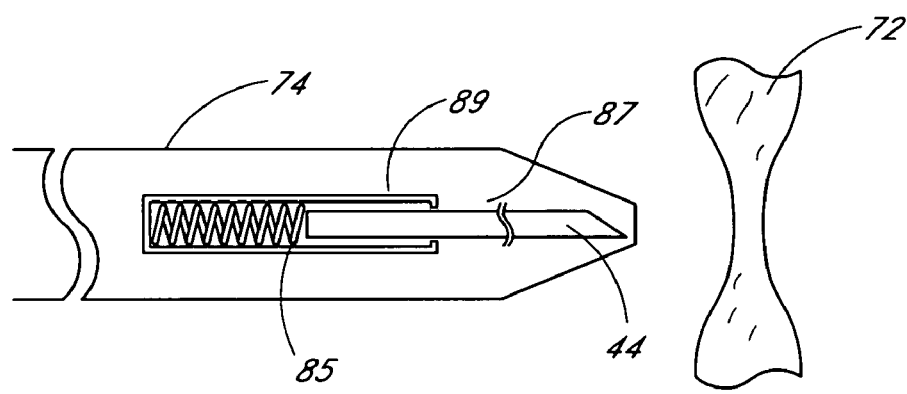
FIGS. 20A and 20B are side views of the needle in accordance with one embodiment of the present invention.
Figure 20B:
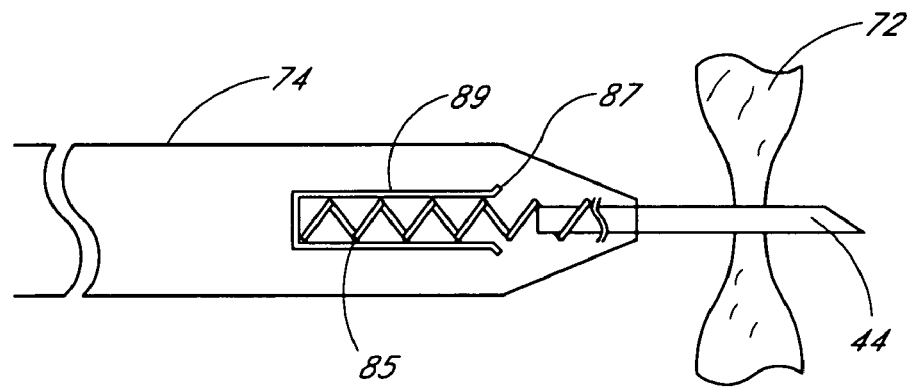

After the tip of the sheath-dilator-transseptal needle combination has been placed in the desired location against the fossa ovalis 72, the transseptal needle 44 is abruptly advanced to accomplish a quick puncture. See FIG. 8. In one embodiment the needle is advanced by applying a force to the proximal end of the needle. In this embodiment the needle often comprises a stiff proximal section and a flexible distal section. The distal section preferably comprises ribbon coil. Alternatively, as illustrated in FIG. 20*a*, the needle 44 is loaded into needle cavity 89 against a distal advancement biasing means 85, such as a spring or coil. The needle 44 is held against the biasing means 85 by a release lock 87. The release lock 87 may comprise any commonly used retaining means, such as corresponding inward and outward projections, grooves or flanges on the needle cavity 89 and the needle 44. The distal end of the sheath 74 is placed in the desired location against the fossa ovalis 72. As illustrated in FIG. 20*b*, the release lock 87 is opened and the biasing means rapidly advances the needle 44 through the fossa ovalis 72. Immediately after the puncture, one medical technique is to confirm the presence of the tip 50 of the transseptal needle 44 within the left atrium 68. Confirmation of such location of the tip 50 of the transseptal needle 44 may be accomplished by monitoring the pressure sensed through the transseptal needle lumen to ensure that the measured pressure is within the expected range and has a waveform configuration typical of left atrial pressure. Alternatively, proper position within the left atrium 68 may be confirmed by analysis of oxygen saturation level of the blood drawn through the transseptal needle 44; i.e., aspirating fully oxygenated blood. Finally, visualization through fluoroscopy alone, or in combination with the use of dye, may also serve to confirm the presence of the tip 50 of the transseptal needle 44 in the left atrium 68.

After placing the transseptal needle tip 50 within the left atrium 68, the tip 27 of the dilator 20 is advanced through the septum 70 and into the left atrium 68. Typically, care is taken to ensure that, at the same time of advancing the dilator and sheath tip into the left atrium, the tip of the transseptal needle is not advanced a sufficient distance that the needle 44 can damage the opposing wall of the left atrium 68. When the tapered tip 27 of dilator 20 appears to have entered the left atrium 68, the transseptal needle 44 is withdrawn. The sheath 74 is then advanced into the left atrium 68, either by advancing the sheath 74 alone over the dilator 20 or by advancing the sheath 74 and dilator 20 in combination. See FIG. 10. The dilator 20 is then withdrawn from sheath 74 when the latter has been advanced into the left atrium, thus leaving the main lumen of sheath 74 as a clear pathway to advancing further diagnostic or therapeutic instruments into the left atrium.

During the initial puncture of the fossa ovalis and the subsequent advancement of the dilator 20 and sheath 74 into the left atrium, it is desirable to minimize "tenting" of the fossa ovalis. The needle 44 is optionally coated with a lubricous material, often a material such as PTFE, hydrophilic material or parylene, preferably PTFE. The dilator 20 is also optionally coated with a lubricous material, often a material such as PTFE, hydrophilic material or parylene, preferably PTFE.

Figure 15A:
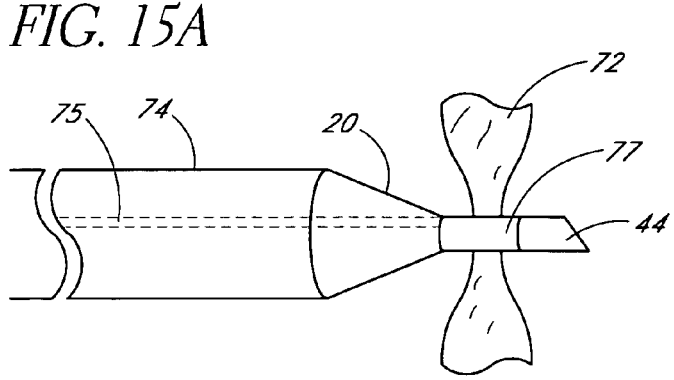
FIGS. 15A–C are side views of a dilator in accordance with one embodiment of the present invention.
Figure 15B:
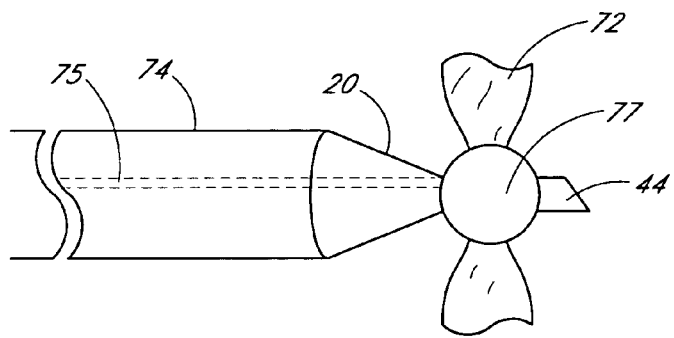
Figure 15C:
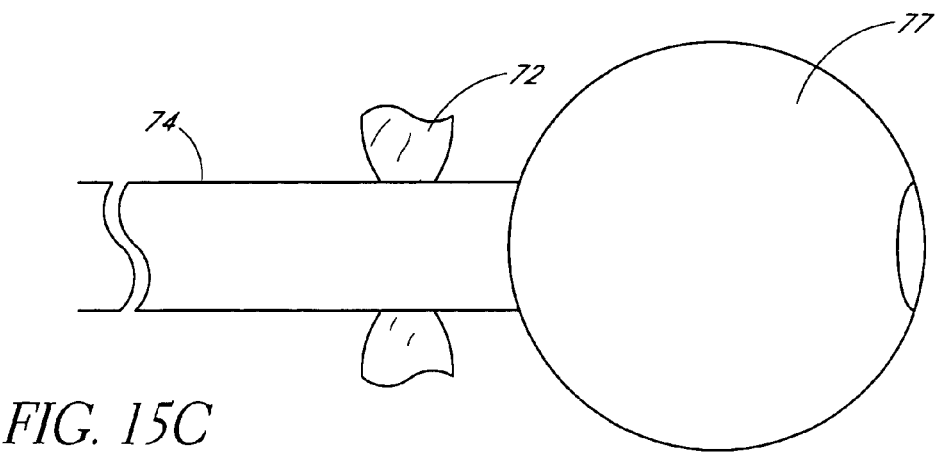

In one embodiment, illustrated in FIGS. 15*a*–15*c*, the sheath 74 contains an inflatable balloon 77 at the distal end and means for inflating the balloon 75, such as an inflation lumen. The balloon 77 is in a deflated position as the needle 44 crosses the fossa ovalis. In one embodiment, illustrated in FIG. 15*b*, the balloon 77 is disposed around the needle 44, and the balloon 77 is inflated as it crosses the fossa ovalis, thereby enlarging the puncture made by the needle 44. This embodiment may be used with or without an additional dilator 20 as described herein. If desired, the balloon 77 may be deflated and withdrawn after the sheath 74 has accessed the left atrium. Alternatively, the balloon may be left inflated, or further inflated after the sheath 74 accesses the left atrium. In another embodiment, as illustrated in FIG. 15*c*, the balloon 77 may be inflated after the balloon crosses the fossa ovalis. In those embodiments where the balloon 77 remains in an inflated position after the sheath 74 crosses the fossa ovalis, the inflated balloon 77 creates an atraumatic distal tip that can be navigated to access a location of interest, such as the LAA. In those embodiments where the balloon 77 is inflated to a diameter greater than the diameter of the sheath 74, the balloon prevents the sheath from unintentionally passing back through the fossa ovalis during subsequent procedures.

Figure 17A:
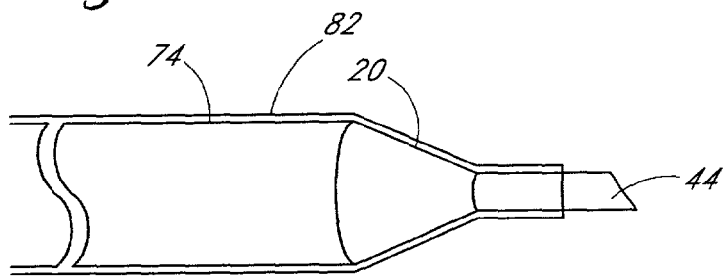
FIGS. 17A–C are side views of the jacket in accordance with one embodiment of the present invention.
Figure 17B:
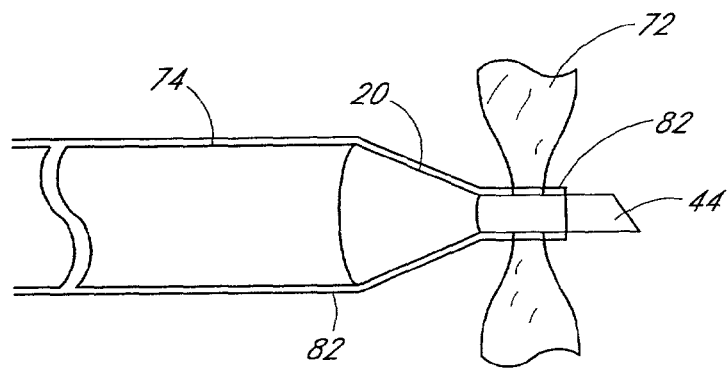
Figure 17C:
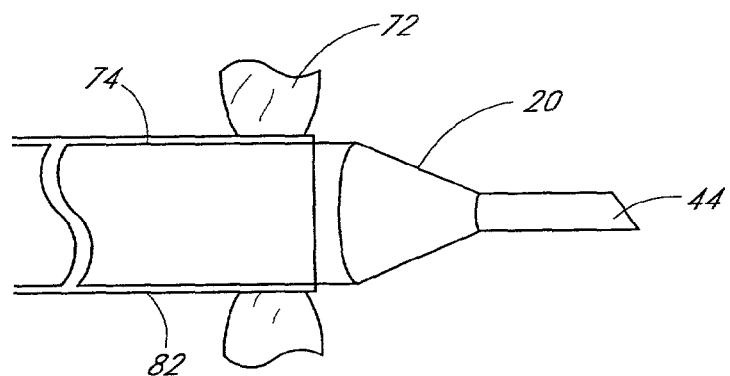

In another embodiment, illustrated in FIGS. 17A, at least a portion of the needle 44, the dilator 20 and at least a distal portion of the sheath 74 are encompassed by a thin-walled jacket 82 that is made of lubricous material, preferably PTFE. As illustrated in FIG. 17B, the distal end of the jacket 82 advances across the fossa ovalis 72 with the needle 44. As illustrated in FIG. 17C, the dilator 20 and sheath 74 then cross the fossa ovalis 72 within the jacket 82. Preferably the jacket is radially enlargeable and may have a thickness in the range of about 0.05 mm to about 0.75 mm depending upon the construction material. The optimum material or combination of materials for coating the needle 44, coating the dilator 20, or forming the jacket 82 can be determined for any particular application through routine experimentation by one or ordinary skill in the art based on the disclosures herein.

Figure 18:
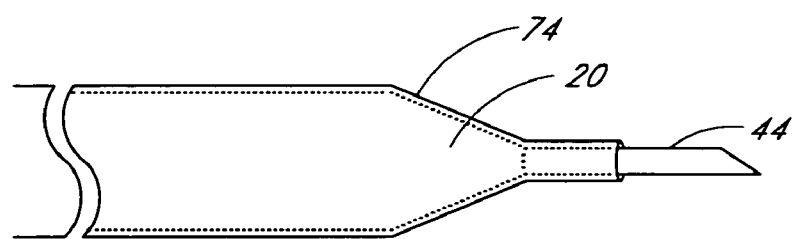
FIG. 18 is a side view of the transseptal access sheath in accordance with one embodiment of the present invention.
Figure 19:
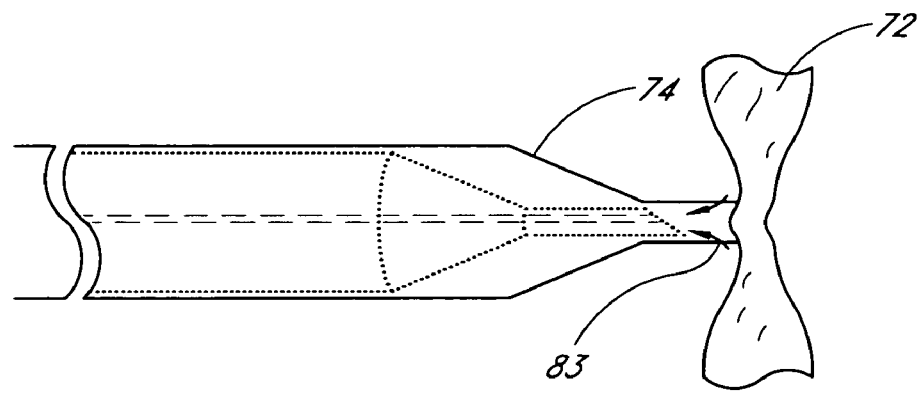
FIG. 19 is a side view of the transseptal access sheath in accordance with one embodiment of the present invention.

In another embodiment, illustrated in FIG. 18, the sheath 74 is itself tapered at its distal end to encompass at least a portion of the dilator. In this embodiment the sheath 74 is preferably tapered to encompass the dilator and at least a portion of the needle 44. In another embodiment, illustrated in FIG. 19, the sheath 74 includes means, such as a vacuum lumen, for applying a vacuum 83 at the distal end. The vacuum lumen may be concentrically disposed within the needle 44 and the dilator 20, concentrically disposed within the dilator 20, but side by side with the needle 44, or side by side with the dilator 20. In one embodiment the vacuum is applied to the fossa ovalis before the needle 44 punctures the fossa ovalis. Alternatively, the vacuum is applied to the fossa ovalis after the needle punctures the fossa ovalis and before or as the dilator 20 crosses the fossa ovalis. The vacuum maintains the position of the fossa ovalis and reduces "tenting" during the transseptal access procedure. Alternatively the vacuum may draw the fossa ovalis into the sheath 74. In yet another embodiment, which one or ordinary skill in the art will appreciate may be used in conjunction with many of the embodiments described above, the needle 44 is oscillated at ultrasonic frequencies to further reduce friction between the needle 44 and the fossa ovalis 72.

Although the present invention has been described in terms of certain preferred embodiments, other embodiments will become apparent to those of skill in the art in view of the disclosure herein. Accordingly, the scope of the present invention is not intended to be limited by the specific embodiments disclosed herein, but, rather, by the full scope of the claims attached below.

What is claimed is:

1. A transseptal access system, comprising a sheath, a dilator and a needle;
   wherein the sheath comprises:
   a first curved section shaped to abut the interior wall of the right atrium substantially opposite the septum and directed toward the septum, and a second curved section shaped to direct a distal end of the sheath toward the left atrial appendage;
   the first curved section having an outer edge that defines
   a first proximal edge point, and
   a first distal edge point
   wherein the intersection between a tangent drawn to the first curved section at the first proximal edge point and a tangent drawn to the first curved section at the first distal edge point, define a first angle and a first plane;
   the second curved section having an outer edge that defines
   a second proximal edge point, and
   a second distal edge point
   wherein the intersection between a tangent drawn to the second curved section at the second proximal edge point and a tangent drawn to the second curved section at the second distal edge point, define a second angle and a second plane;
   wherein the first angle is within the range of about 75 degrees to about 105 degrees;
   wherein the second angle is within the range of about 75 degrees to about 105 degrees;
   wherein the angle between the first and second plane is within the range of about 75 degrees to about 105 degrees;
   wherein the needle is coated with PTFE.

2. The transseptal access system of claim 1, wherein the first angle is within the range of about 80 degrees to about 100 degrees.

3. The transseptal access system of claim 1, wherein the second angle is within the range of about 80 degrees to about 100 degrees.

4. The transseptal access system of claim 1, wherein the dilator comprises an inflatable balloon.

5. The transseptal access system of claim 1, wherein the dilator comprises a spiral helical structure.

6. The transseptal access system of claim 1, wherein the dilator is coated with PTFE.

7. The transseptal access system of claim 1, wherein the needle is advanced by a biasing means.

8. A transseptal access system, comprising a sheath, a dilator and a needle;
   wherein the sheath comprises:
   a first curved section shaped to abut the interior wall of the right atrium substantially opposite the septum and directed toward the septum, and a second curved section shaped to direct a distal end of the sheath toward the left atrial appendage;
   the first curved section having an outer edge that defines
   a first proximal edge point, and
   a first distal edge point
   wherein the intersection between a tangent drawn to the first curved section at the first proximal edge point and a tangent drawn to the first curved section at the first distal edge point, define a first angle and a first plane;
   the second curved section having an outer edge that defines
   a second proximal edge point, and
   a second distal edge point
   wherein the intersection between a tangent drawn to the second curved section at the second proximal edge point and a tangent drawn to the second curved section at the second distal edge point, define a second angle and a second plane;
   wherein the first angle is within the range of about 75 degrees to about 105 degrees;
   wherein the second angle is within the range of about 75 degrees to about 105 degrees;
   wherein the angle between the first and second plane is within the range of about 75 degrees to about 105 degrees;
   wherein the dilator comprises a vacuum lumen to allow application of a vacuum to the fossa ovalis.

9. The transseptal access system of claim 8, wherein the first angle is within the range of about 80 degrees to about 100 degrees.

10. The transseptal access system of claim 8, wherein the second angle is within the range of about 80 degrees to about 100 degrees.

11. A transseptal access system, comprising a sheath, a dilator and a needle;
    wherein the sheath comprises:
    a first curved section shaped to abut the interior wall of the right atrium substantially opposite the septum and directed toward the septum, and a second curved section shaped to direct a distal end of the sheath toward the left atrial appendage;
    the first curved section having an outer edge that defines
    a first proximal edge point, and
    a first distal edge point
    wherein the intersection between a tangent drawn to the first curved section at the first proximal edge point and a tangent drawn to the first curved section at the first distal edge point, define a first angle and a first plane;
    the second curved section having an outer edge that defines
    a second proximal edge point, and
    a second distal edge point
    wherein the intersection between a tangent drawn to the second curved section at the second proximal edge point and a tangent drawn to the second curved section at the second distal edge point, define a second angle and a second plane;
    wherein the first angle is within the range of about 75 degrees to about 105 degrees;
    wherein the second angle is within the range of about 75 degrees to about 105 degrees;
    wherein the angle between the first and second plane is within the range of about 75 degrees to about 105 degrees;
    wherein the dilator includes at least one infusion port for infusing saline solution.

12. The transseptal access system of claim 11, wherein the first angle is within the range of about 80 degrees to about 100 degrees.

13. The transseptal access system of claim 11, wherein the second angle is within the range of about 80 degrees to about 100 degrees.

14. The transseptal access system of claim 11, wherein the dilator is coated with PTFE.

15. The transseptal access system of claim 11, wherein the needle is advanced by a biasing means.

16. A transseptal access system, comprising a sheath, a dilator and a needle;

wherein the sheath comprises:
a first curved section shaped to abut the interior wall of the right atrium substantially opposite the septum and directed toward the septum, and a second curved section shaped to direct a distal end of the sheath toward the left atrial appendage;
the first curved section having an outer edge that defines
a first proximal edge point, and
a first distal edge point
wherein the intersection between a tangent drawn to the first curved section at the first proximal edge point and a tangent drawn to the first curved section at the first distal edge point, define a first angle and a first plane;
the second curved section having an outer edge that defines
a second proximal edge point, and
a second distal edge point
wherein the intersection between a tangent drawn to the second curved section at the second proximal edge point and a tangent drawn to the second curved section at the second distal edge point, define a second angle and a second plane;
wherein the first angle is within the range of about 75 degrees to about 105 degrees;
wherein the second angle is within the range of about 75 degrees to about 105 degrees;
wherein the angle between the first and second plane is within the range of about 75 degrees to about 105 degrees;
wherein the sheath comprises a vacuum lumen to allow application of a vacuum to the fossa ovalis.

17. The transseptal access system of claim 16, wherein the first angle is within the range of about 80 degrees to about 100 degrees.

18. The transseptal access system of claim 16, wherein the second angle is within the range of about 80 degrees to about 100 degrees.

19. A transseptal access system, comprising a sheath, a dilator and a needle;
wherein the sheath comprises:
a first curved section shaped to abut the interior wall of the right atrium substantially opposite the septum and directed toward the septum, and a second curved section shaped to direct a distal end of the sheath toward the left atrial appendage;
the first curved section having an outer edge that defines
a first proximal edge point, and
a first distal edge point
wherein the intersection between a tangent drawn to the first curved section at the first proximal edge point and a tangent drawn to the first curved section at the first distal edge point, define a first angle and a first plane;
the second curved section having an outer edge that defines
a second proximal edge point, and
a second distal edge point
wherein the intersection between a tangent drawn to the second curved section at the second proximal edge point and a tangent drawn to the second curved section at the second distal edge point, define a second angle and a second plane;
wherein the first angle is within the range of about 75 degrees to about 105 degrees;
wherein the second angle is within the range of about 75 degrees to about 105 degrees;
wherein the angle between the first and second plane is within the range of about 75 degrees to about 105 degrees;
wherein the needle has a spiral helical structure.

20. The transseptal access system of claim 19, wherein the first angle is within the range of about 80 degrees to about 100 degrees.

21. The transseptal access system of claim 19, wherein the second angle is within the range of about 80 degrees to about 100 degrees.

22. A transseptal access system comprising a sheath, a dilator and a needle;
wherein the sheath comprises:
a first curved section shaped to abut the interior wall of the right atrium substantially opposite the septum and directed toward the septum, and a second curved section shaped to direct a distal end of the sheath toward the left atrial appendage;
the first curved section having an outer edge that defines
a first proximal edge point, and
a first distal edge point
wherein the intersection between a tangent drawn to the first curved section at the first proximal edge point and a tangent drawn to the first curved section at the first distal edge point, define a first angle and a first plane;
the second curved section having an outer edge that defines
a second proximal edge point, and
a second distal edge point
wherein the intersection between a tangent drawn to the second curved section at the second proximal edge point and a tangent drawn to the second curved section at the second distal edge point, define a second angle and a second plane;
wherein the first angle is within the range of about 75 degrees to about 105 degrees;
wherein the second angle is within the range of about 75 degrees to about 105 degrees;
wherein the angle between the first and second plane is within the range of about 75 degrees to about 105 degrees; and
an ultrasound transducer for oscillating the needle at ultrasonic frequencies.

23. The transseptal access system of claim 22, wherein the first angle is within the range of about 80 degrees to about 100 degrees.

24. The transseptal access system of claim 22, wherein the second angle is within the range of about 80 degrees to about 100 degrees.

25. A transseptal access system, comprising a sheath, a dilator and a needle;
wherein the sheath comprises:
a first curved section shaped to abut the interior wall of the right atrium substantially opposite the septum and directed toward the septum, and a second curved section shaped to direct a distal end of the sheath toward the left atrial appendage;
the first curved section having an outer edge that defines
a first proximal edge point, and
a first distal edge point
wherein the intersection between a tangent drawn to the first curved section at the first proximal edge point and a tangent drawn to the first curved section at the first distal edge point, define a first angle and a first plane;
the second curved section having an outer edge that defines a second proximal edge point, and
a second distal edge point
wherein the intersection between a tangent drawn to the second curved section at the second proximal edge point and a tangent drawn to the second curved section at the second distal edge point, define a second angle and a second plane;
wherein the first angle is within the range of about 75 degrees to about 105 degrees;
wherein the second angle is within the range of about 75 degrees to about 105 degrees;
wherein the angle between the first and second plane is within the range of about 75 degrees to about 105 degrees;

wherein the needle has at least one expandable cutting surface.

26. The transseptal access system of claim 25, wherein the first angle is within the range of about 80 degrees to about 100 degrees.

27. The transseptal access system of claim 25, wherein the second angle is within the range of about 80 degrees to about 100 degrees.

* * * * *